(12) United States Patent
Anselmo Viegas Garcia et al.

(10) Patent No.: US 11,168,179 B2
(45) Date of Patent: Nov. 9, 2021

(54) MACROMOLECULAR TRANSITION METAL COMPLEXES FOR TREATMENT OF CANCER AND PROCESS FOR THEIR PREPARATION

(71) Applicant: FACULDADE DE CIÊNCIAS DA UNIVERSIDADE DE LISBOA, Lisbon (PT)

(72) Inventors: Maria Helena Anselmo Viegas Garcia, Lisbon (PT); Andreia Marques Valente, Avanca (PT); Tânia Sofia Ferreira Morais, Ericeira (PT); Ana Isabel Antunes Tomaz Diniz, Queluz (PT)

(73) Assignee: FACULDADE DE CIÊNCIAS DA UNIVERSIDADE DE LISBOA, Lisbon (PT)

( * ) Notice: Subject to any disclaimer, the term of this patent is extended or adjusted under 35 U.S.C. 154(b) by 91 days.

(21) Appl. No.: 15/533,289

(22) PCT Filed: Dec. 7, 2015

(86) PCT No.: PCT/IB2015/002312
§ 371 (c)(1),
(2) Date: Jun. 5, 2017

(87) PCT Pub. No.: WO2016/087932
PCT Pub. Date: Jun. 9, 2016

(65) Prior Publication Data
US 2018/0009940 A1    Jan. 11, 2018

(30) Foreign Application Priority Data

Dec. 6, 2014 (PT) .......................................... 108082

(51) Int. Cl.
| | | |
|---|---|---|
| *C08G 63/91* | (2006.01) | |
| *C07F 15/00* | (2006.01) | |
| *C07D 213/22* | (2006.01) | |
| *C07F 9/50* | (2006.01) | |
| *C07F 15/02* | (2006.01) | |
| *A61K 31/787* | (2006.01) | |

(52) U.S. Cl.
CPC .......... *C08G 63/912* (2013.01); *A61K 31/787* (2013.01); *C07D 213/22* (2013.01); *C07F 9/5004* (2013.01); *C07F 9/5022* (2013.01); *C07F 15/0046* (2013.01); *C07F 15/02* (2013.01)

(58) Field of Classification Search
CPC ...... C08G 63/912; C07F 15/02; C07F 9/5004; C07F 9/5022; C07F 15/0046; C07D 213/22; A61K 31/787
See application file for complete search history.

(56) References Cited

PUBLICATIONS

Miao Acees to new carbohydrate functionalized polylactides, Polymer, p. 5018 (Year: 2011).*

Andreia Valente, Maria Helena Garcia, Fernanda Marques, Yong Miao, Cyril Rousseau, Philippe Zinck, First polymer "ruthenium-cyclopentadienyl" complex as potential anticancer agent, Journal of Inorganic Biochemistry, 2013, pp. 79-81, issue No. 127, www.elsevi er.com/ locate/ jinorgb.

Ning Liu, Chun Liu, Zilin Jin, Green synthesis of fluorinated biaryl derivatives via thermoregulated ligand/palladium-catalyzed Suzuki reaction, Journal of Inorganic Biochemistry, 2011, pp. 2641-2647, issue No. 696, www.elsevier.com/locate/jorganchem.

Elke David, Roland Born, Evgeny Kaganer, Ernesto Joselevich, Heinz Dürr, and Itamar Willner, Photoinduced Electron Transfer in Supramolecular Assemblies Composed of One-Shell and Two-Shell Dialkoxybenzene-Tethered Ru(II)-Tris(bipyridine) Derivatives and a Bipyridinium Cyclophane, J. Am. Chem. Soc., 1997, issue No. 119, pp. 7778-7790.

Ana Cristina Gorncalves,Tania S. Morais, M. Paula Robalo, Fernanda Marques, Fernando Avecilla, Cristina P. Matos, Isabel Santos, Ana Isabel Tomaz, M. Helena Garcia, Important cytotoxicity of novel iron(II) cyclopentadienyl complexes with imidazole based ligands, Journal of Inorganic Biochemistry, 2013, pp. 1-8, issue 129, www.elsevi er.com/ locate/ jinorgb.

Yi-Hsien Liao and John R. Moss, Ruthenium-containing Organometallic Dendrimers, J. Chem. Soc., Chem. Commun., 1993, pp. 1774-1777.

Kai Cao, Jonathan Ward, Ryan C. Amos, Moon Gon Jeong, Kyoung Taek Kim, Mario Gauthier, Daniel Foucher, Xiaosong Wang, Organometallic macromolecules with piano stool coordination repeating units: chain configuration and stimulated solution behavior, The Royal Society of Chemistry, 2014, pp. 10062-10065, issue 50, www.rsc.org/chemcomm.

International Search Report for PCT/IB2015/002312 Completed Jun. 27, 2017; dated Jul. 6, 2016 6 pages.

Written Opinion for PCT/IB2015/002312 Completed Jun. 27, 2017; dated Jul. 6, 2016 6 pages.

* cited by examiner

*Primary Examiner* — Matthew P Coughlin
*Assistant Examiner* — Thurman Wheeler
(74) *Attorney, Agent, or Firm* — The Roy Gross Law Firm, LLC; Roy Gross

(57) ABSTRACT

The present invention relates to macromolecular transition metal complexes, characterized by having the general formula (I), to the process for their preparation, and to bidentate and monodentate macroligands. The invention also refers to pharmaceutical compositions and medicaments containing said macromolecular transition metal complexes, and to the use of said pharmaceutical compositions, medicaments and macromolecular transition metal complexes for cancer therapy and/or cancer prevention, as antitumor agent in solid tumors, liquid tumors and/or metastases and/or as radiosensitizer agents.

6 Claims, 12 Drawing Sheets

MACROMOLECULAR TRANSITION METAL COMPLEXES FOR TREATMENT OF CANCER AND PROCESS FOR THEIR PREPARATION

CROSS REFERENCE TO RELATED APPLICATIONS

This application is a National Stage Entry under 371 of PCT/IB2015/002312 filed on Dec. 7, 2015 claiming priority to Portugal Application No. 108082 filed Dec. 6, 2014. The contents of both applications are incorporated by reference herein in their entirety.

TECHNICAL FIELD

The present invention relates to macromolecular transition metal complexes, to pharmaceutical compositions containing them, to their use in medicament, particularly as antitumor and antimetastatic agents, as well as to the process for their preparation.

BACKGROUND ART

Metal complexes are currently recognised as an emerging class of potentially very effective agents for treating cancer.

A. Valente, M. H. Garcia, F. Marques, Y. Miao, C. Rousseau, P. Zinck, "First polymer 'ruthenium-cyclopentadienyl' complex as potential anticancer agent", Journal of Inorganic Biochemistry 2013, 127, 79-81 describe a class of ruthenium compounds synthesized using methyl 2,3,4-tri-O-benzyl-α-D-glucopyranoside (a molecule of biologic interest) as initiator for the polymerization of the lactide catalysed by dimethylaminopyridine, leading to a polylactide functionalized at the chain end with a substituted. D-glucose; thereafter, this polymer was reacted with 2,2'-bipyridine-4,4' dicarbonyl dichloride leading to the macroligand that contains an ester attached to each of the rings of the bipyridine, with approximately 75% purity. The final compound results from the synthesis between this macroligand and $[Ru(\eta^5-C_5H_5)(PPh_3)_2Cl]$ in the presence of silver triflate in dichloromethane.

WO 2007/128158 A1 (DYSON, Paul, Joseph et al) discloses transition metal complexes for inhibiting resistance in the treatment of cancer and metastasis. This patent application encompasses several families of transition metal complexes; yet, it does not disclose complexes with macroligands in its constitution.

Organometallic compounds for the treatment of cancer are disclosed in EP patent application 07101258.7; however, no indication of compounds containing macromolecular ligands is given or disclosed therein.

In the review article "Polymer-Metal Complexes (PMC) for Cancer Therapy" (A. Valente, P. Zinck, Recent Research Developments in Polymer Science, 11 (2012):99-128, published by Transworld Research Network, Trivandrum, India (ISBN: 978-81-7895-538-4)), the main families of compounds containing polymers in its constitution are referred to. Most of them have been reported using platinum as the central metal and without using the cyclopentadienyl ligand. The vast majority of the approaches are multinuclear, i.e., each molecule of compound presents several metal centres in its constitution.

The review article on macromolecular compounds of ruthenium "Syntheses of macromolecular ruthenium compounds: a new approach to the search of anticancer drugs" (A. Valente, M. H. Garcia, Inorganics 2014, 2, 96-114) refers approaches to cancer therapy using ruthenium macromolecular compounds. All the strategies found in the literature are multinuclear approaches and the only disclosure that contemplates the cyclopentadienyl ligand is the above referred article (A. Valente, M. H. Garcia, F. Marques, Y. Miao, C. Rousseau, P. Zinck, "First polymer 'ruthenium-cyclopentadienyl' complex as potential anticancer agent", Journal of Inorganic Biochemistry 2013, 127, 79-81). Advantageously, the complexes of the present invention are mononuclear (i.e. contain only one metal atom per molecule), which allows a precise control of the amount of drug to administer.

The development of effective methods by which drugs are administered and delivered to the target is as important in the fight against cancer as the efficiency of the drug itself.

In addition, there is a need for compounds that are therapeutically more effective and also able to overcome chemotherapy side effects caused by the drugs currently available.

Several approaches of treatment with multinuclear macromolecular metal compounds present the problem of the administration in an approximate percentage of metal for a certain amount of drug, and therefore a great need is felt for greater accuracy and control over the amount of metal being administered.

Another felt need is the stability of the new compounds in aqueous medium.

The present invention provides new metal complexes and new drugs, as well as pharmaceutical compositions containing them, which can be delivered to cancer cells with high efficiency and precision, due to the inclusion of macroligands and/or molecules of biological interest in the sphere of coordination of the metals used.

The new complexes of the present invention include a polymeric ligand and, consequently, they exhibit a high molecular weight. This feature allows to profit from an enhanced permeation and retention in the tumor tissues, which results in a preferential accumulation of the complex in these tissues compared to that which can occur in healthy tissues ("*enhanced permeation and retention effect*", EPR *effect*—J. Kopecek, P. Kopeckova, T. Minko, Z. R. Lu, "HPMA copolymer-anticancer drug conjugates: design, activity, and mechanism of action", 2000, Eur. J. Pharm. Biopharm; Y. Matsumura, H. Maeda, "A New Concept for Macromolecular Therapeutics in Cancer Chemotherapy: Mechanism of Tumoritropic Accumulation of Proteins and the Antitumor Agent Smancs", 1986, Cancer Res.) This is possible since the tumors, with very rapid and abnormal cell growth, have deficient vascularization, allowing the molecules with high molecular mass to penetrate within the cells, but have difficulty in leaving, so that over time there is a greater accumulation in the tumor tissue. Thus, a drastic reduction of side effects can be obtained when compared with the molecules with a low molecular weight, that can freely come in and out from tumor tissues (S. Parveen, R. Misra, S. K. Sahoo, "Nanoparticles: a boon to drug delivery, therapeutics, diagnostics and imaging", 2012, Nanomedicine: Nanotechnology, Biology and Medicine).

The present invention also provides new syntheses of macromolecular transition metal complexes, including macromolecules and metallodrugs. In addition, the syntheses of the present invention provide molecules of the compounds of the present invention with a controlled accurate amount of metal, with a degree of purity of 80-95%, and consequently such compounds are suitable for controlled administration.

The results gathered indicate that both the macromolecular compounds of the present invention when administered and their fragments originated in the specific conditions found in the tumor maintain the desired cytotoxic activity.

The compounds of the present invention are stable in air and in aqueous medium for periods adequate to their use as medicaments and they present an enhanced cytotoxicity compared to the drug in clinical use, cisplatin. These are important and advantageous features when the development of new drugs is pursued.

The new class of compounds object of the present invention have application in the treatment of cancer, both of the primary tumor and of the metastases it originated.

As the compounds of the present invention absorb visible light, they can also generate reactive oxygen species in the excited state (singlet), and be used in photodynamic therapy for treating superficial cancers as those of the skin and pharynx, among others.

Pharmaceutical compositions are an object of the present invention. The complexes and compositions according to the invention can be used for example as medicaments in the treatment of tumors, both of the primary tumor and of the metastases it originated, including in photodynamic therapy for treating superficial cancers as cancers of the skin and the pharynx, among others.

Such complexes and compositions are intended for use via topical, intravenous, subcutaneous and intraperitoneal administration.

These and other advantages of the present invention will become more apparent apparent and will be better understood from the following description, claims and appended drawings.

Additional objectives, advantages and characteristics will become apparent to those ordinarily skilled in the art by the analysis of the description or the practice of the invention.

Throughout the description and the claims, the words "comprise" and "include" and their variations should not be understood as excluding other technical features or components.

SUMMARY OF INVENTION

The present invention has been accomplished in order to overcome the disadvantages referred to in the state of the art, and it is an object of the present invention to provide macromolecular transition metal complexes characterized by having the general formula (I):

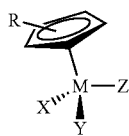

(I)

represented by the molecular formula [M(CpR)XYZ], wherein:

M is ruthenium, iron, rhodium, iridium or osmium;

CpR is cyclopentadienyl wherein R is H, or substituted cyclopentadienyl, R being selected from: a biomolecule, preferably selected from amino acids, peptides, oligopeptides, proteins, protein fragments, estradiol and its derivatives, vitamins, carbohydrates, water, nucleic acids, a heteroaromatic ligand, a bioactive compound or a radical —$R_1$, —$R_1$—$NH_2$, —$R_1$—CCOH, —$R_1$—COO—, —R1-OH, —$R_1$—$COONCH_3$, wherein $R_1$ is an alkyl or aryl group; the R groups can be bonded to the cyclopentadienyl ring at any of the ring carbons. R can occupy more than one carbon atom, which can lead to a cyclopentadienyl ring substituted in the positions 1, 2, 3, 4 and/or 5;

one of the X, Y or Z ligands is a macroligand, which can itself be a heteroaromatic ligand, X, Y and Z can be selected from heteroaromatic ligands, macroligands, CO, dimethyl sulfoxide, a biomolecule or a molecule of biological interest, preferably selected from sugars, estrogen, molecules comprising conjugated π systems, under the following conditions:

at least one of X, Y or Z is a heteroaromatic ligand, CO or dimethyl sulfoxide; and at least one of the X, Y or Z ligands comprises or is a biomolecule or a molecule of biological interest;

and one of the following conditions:

X, Y and Z are any suitable monodentate ligands, preferably selected from phosphanes; heteroaromatic molecules wherein the heteroatom can be any suitable heteroatom, and is preferably selected from O, S, P, N or Se; CO; dimethyl sulfoxide; acetonitrile; nitriles; isonitriles; dimethylformamide; a biomolecule or a molecule of biological interest and at least one of X, Y or Z includes a macroligand; or X and Y together represent any suitable bidentate macroligand preferably selected from macromolecular diphosphanes, macromolecular heteroaromatic molecules having at least one methyleneoxy or aminooxy function at the heteroaromatic ring(s), macromolecular oxalates or macromolecular glycinates and Z is any suitable monodentate ligand preferably selected from phosphanes, heteroaromatic molecules wherein the heteroatom can be any suitable heteroatom and is preferably selected from O, S, P, N or Se; CO; dimethyl sulfoxide; acetonitrile; nitriles; isonitriles; or dimethylformamide;

X and Y together represent any suitable bidentate ligand preferably selected from diphosphanes, heteroaromatic molecules, oxalates, glycinates, trimethylethylenediamine, ethylenediamine, a biomolecule or a molecule of biological interest, and Z is any suitable monodentate ligand preferably selected from macromolecular phosphanes, macromolecular heteroaromatic molecules wherein the heteroatom can be any suitable heteroatom and is preferably selected from O, S, P, N or Se; macromolecular nitriles; or macromolecular isonitriles.

and pharmacologically acceptable salts thereof.

The macroligands, the macromolecular monodentate ligands and the macromolecular bidentate ligands are molecules with a molecular weight >1000 g/mol, natural or synthetic, having linear or branched chain, comprising a repeating unit, and having at least at one of its chain ends one or more functional groups allowing their coordination to a metal center and optionally having at one of its chain ends biomolecules, preferably selected from amino acids, peptides, oligopeptides, proteins, protein fragments, estradiol and its derivatives, vitamins, carbohydrates, water, nucleic acids, or molecules of biological interest. In an embodiment the macroligands are natural or synthetic polymers having linear or branched chain, containing one or more repeating units preferably selected from polylactide, polycaprolactone, poly-N-(2-hydroxypropyl)methacrylamide, poly(γ,L-glutamic acid), poly(citric acid), poly(ethylene glycol), poly(aspartic acid); copolymers preferably selected from poly(γ, L-glutamic acid)-citric acid, poly(ethylene glycol)-block-poly(glutamic acid), poly(ethylene glycol)-block-poly(aspartic acid), poly(ethylene glycol)-block-poly(lactic acid), poly(ethylene glycol)-poly(caprolactone); or biopolymers, natural or synthetic, preferably selected from cellulose, starch, chitin, proteins, peptides, DNA and RNA.

Metal salts are halide, nitrite, phosphate, perchlorate or carbonate salts.

In one aspect, it is an object of the present invention to provide bidentate macroligands of general formula (XIV):

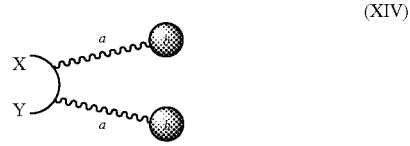

monodentate macroligands of general formula (XV):

as defined in the attached claims.

In another aspect, the synthetic procedure for the complexes of the present invention, including that of macroligands, is an object of the present invention as defined in the attached claims.

Other objects of the present invention are pharmaceutical compositions and medicaments comprising a pharmaceutically effective amount of at least one macromolecular organometallic complex of a transition metal of formula (I), (II), (III) or (IV), as well as its use as a medicament, optionally with other active ingredients and/or pharmaceutically acceptable vehicles and/or excipients, as defined in the attached claims.

As defined in the attached claims, the macromolecular organometallic complexes of transition metal and the pharmaceutical compositions containing them, in accordance with the present invention, can be used as antitumor agents and/or as radiosensitizer agents for cancer therapy and/or cancer prevention, in particular for use in the treatment of solid tumors, liquid tumors and/or metastases. The route of administration can be topical, intravenous, subcutaneous or intraperitoneal.

These and other advantages of the present invention will be apparent and will be better understood from the following description and appended drawings and claims. However, the following examples and drawings are provided to illustrate the inventive concepts and are not intended to limit the scope of the invention.

DETAILED DESCRIPTION OF THE INVENTION

Figure 1:
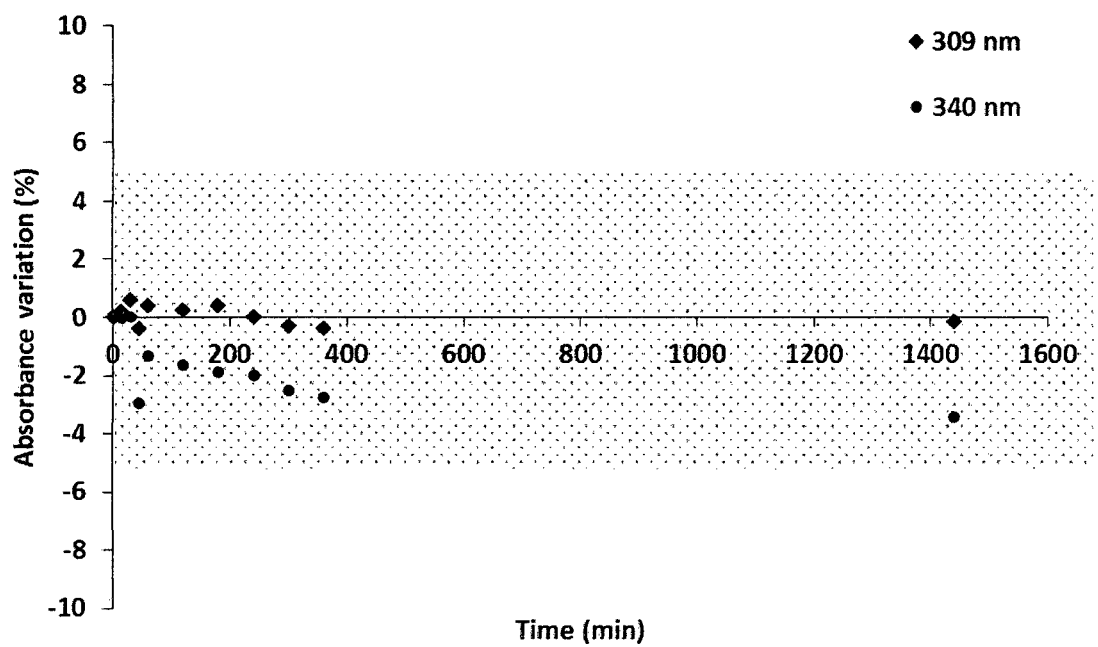
FIGS. 1a) to 1f) are graphs showing the chemical stability in aqueous medium of the compounds 1, 2, 3, 4, 5 and 6, respectively.
Figure 1:
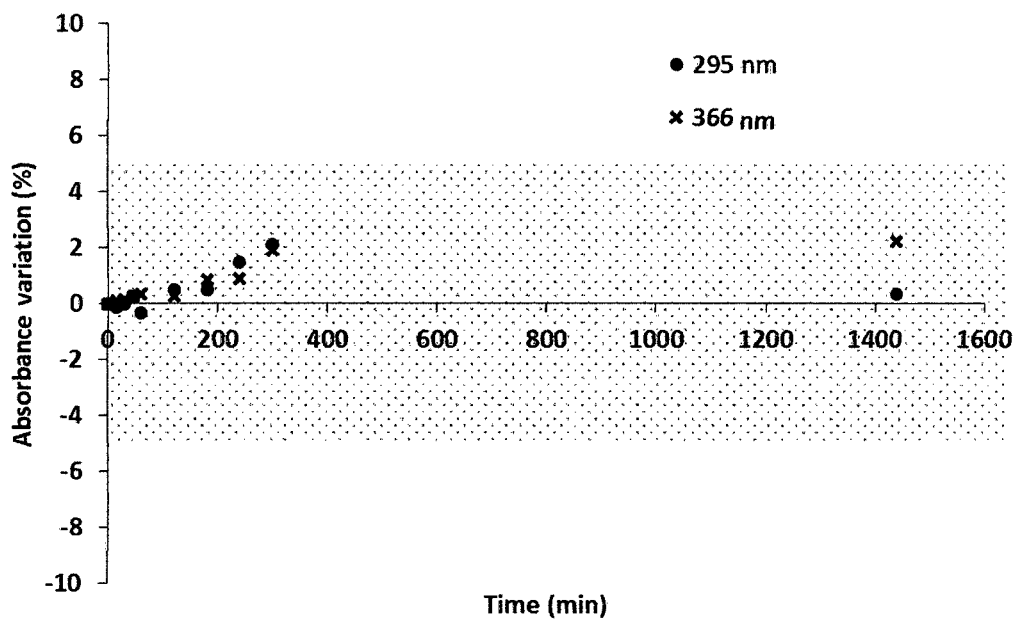
Figure 1:
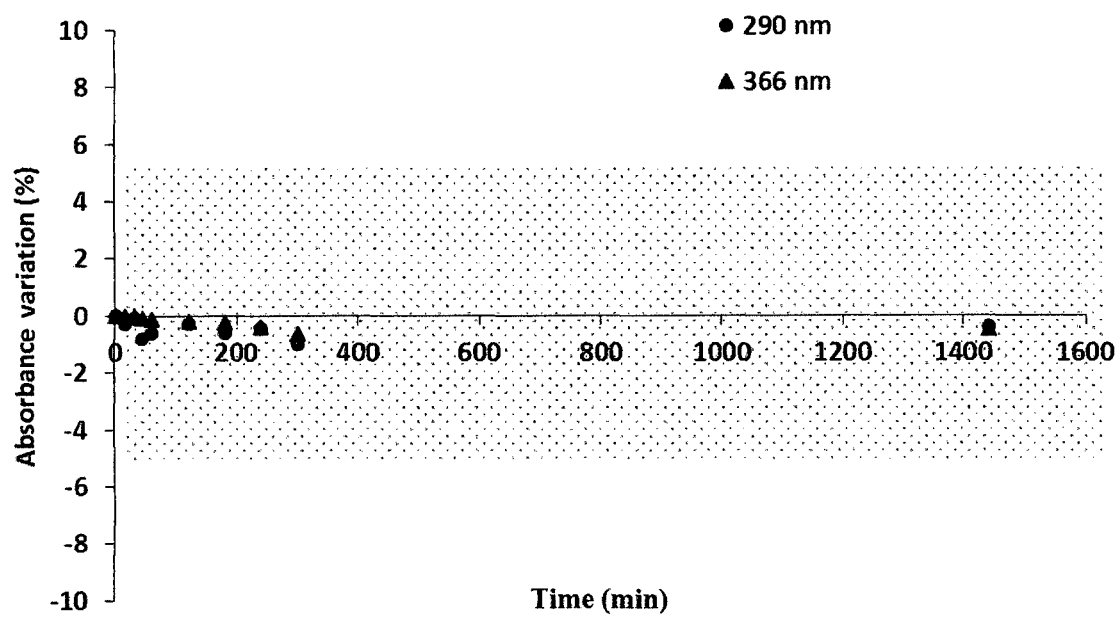
Figure 1:
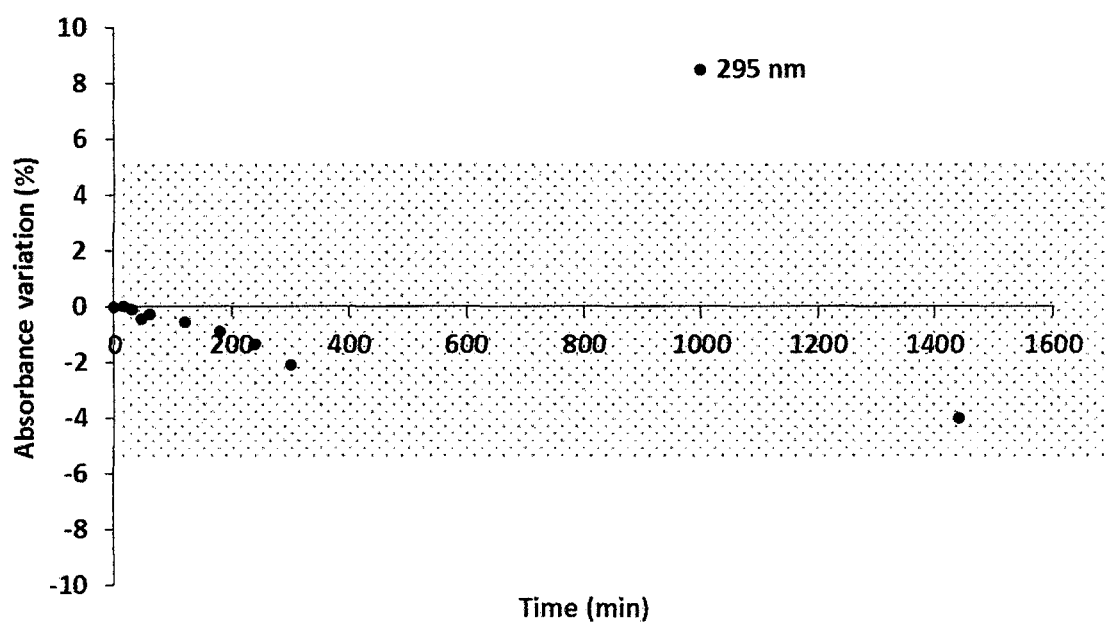
Figure 1:
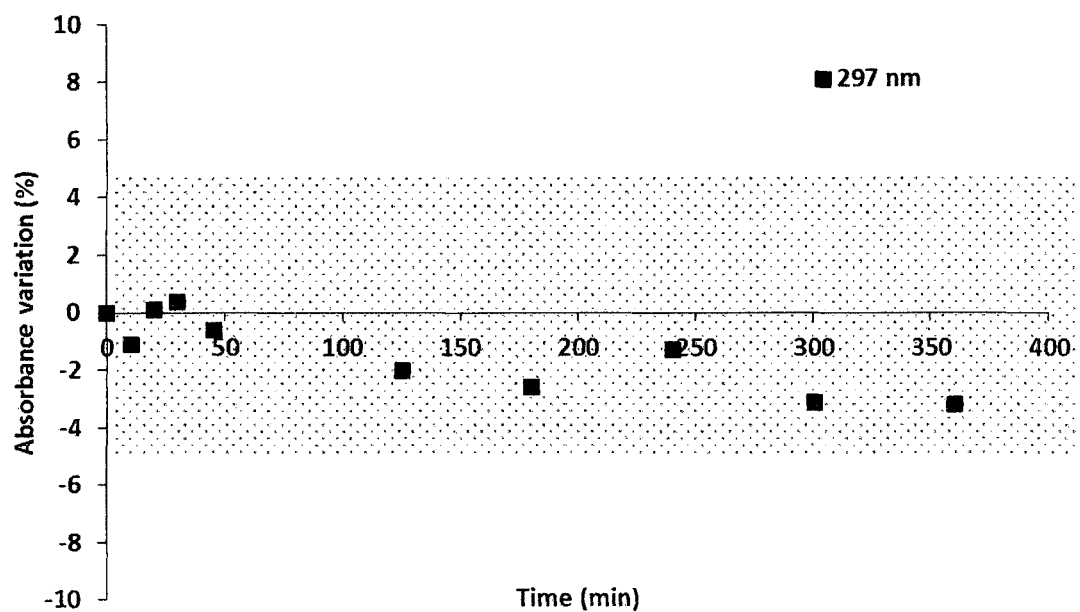
Figure 1:
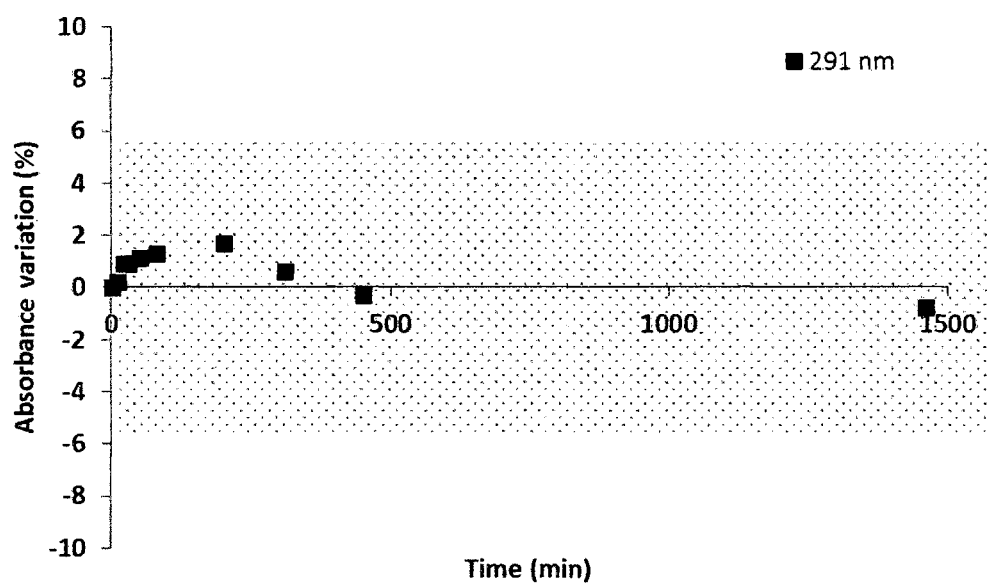
Figure 2:
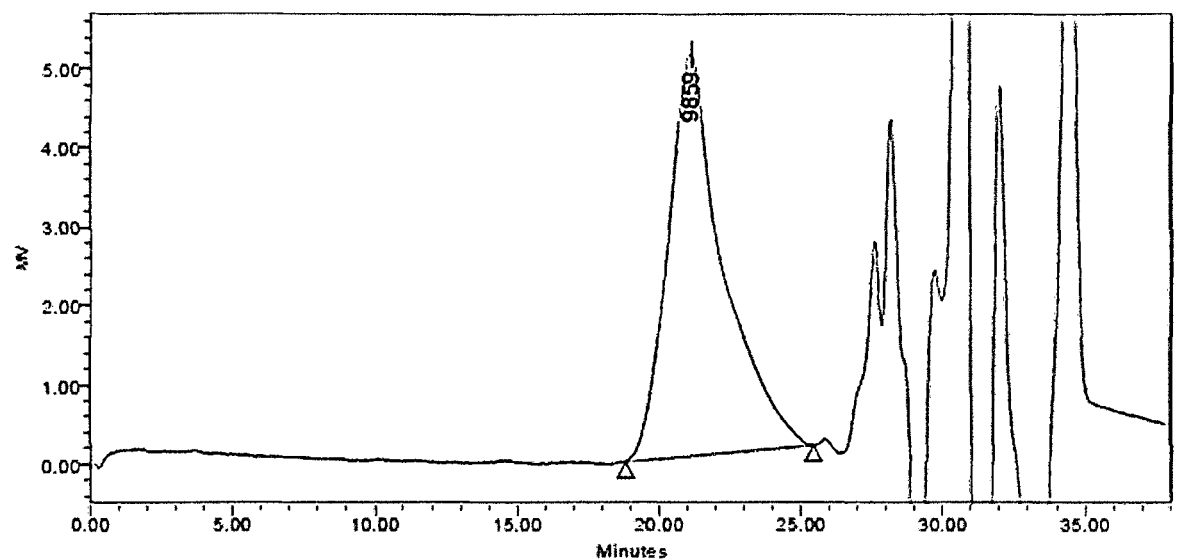
FIGS. 2a) to 2f) are graphs showing the results of gel permeation chromatography for the compounds 1, 2, 3, 4, 5 and 6, respectively.
Figure 2:
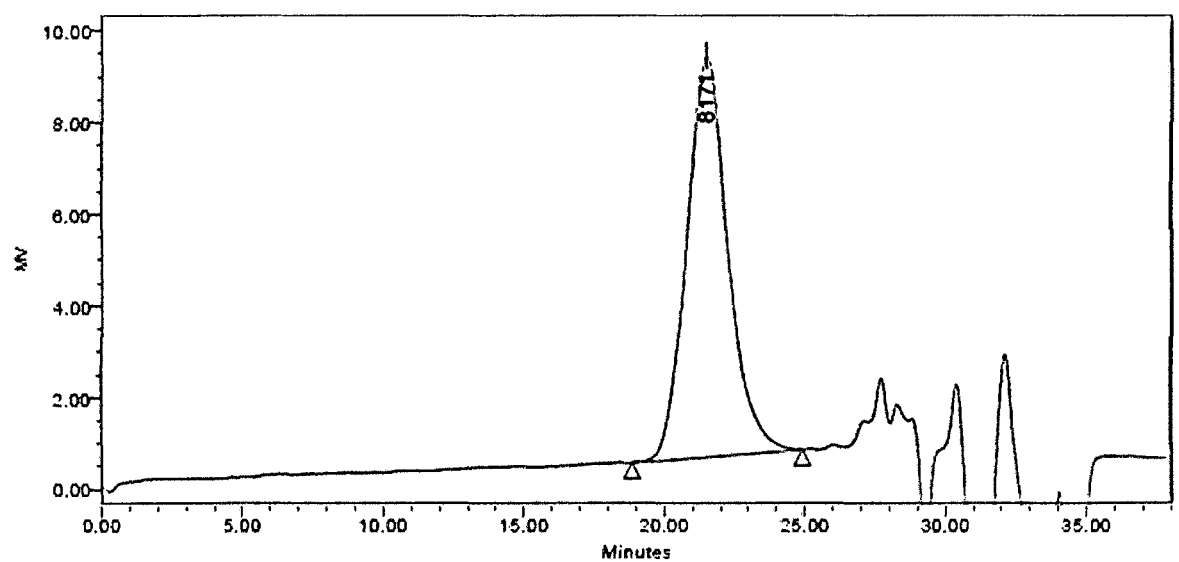
Figure 2:
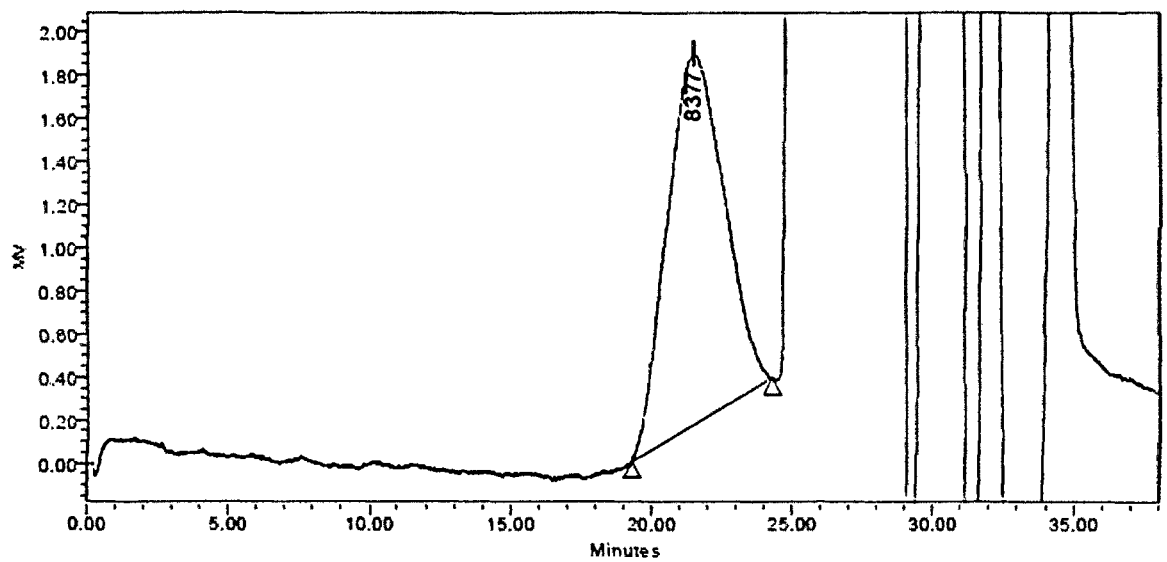
Figure 2:
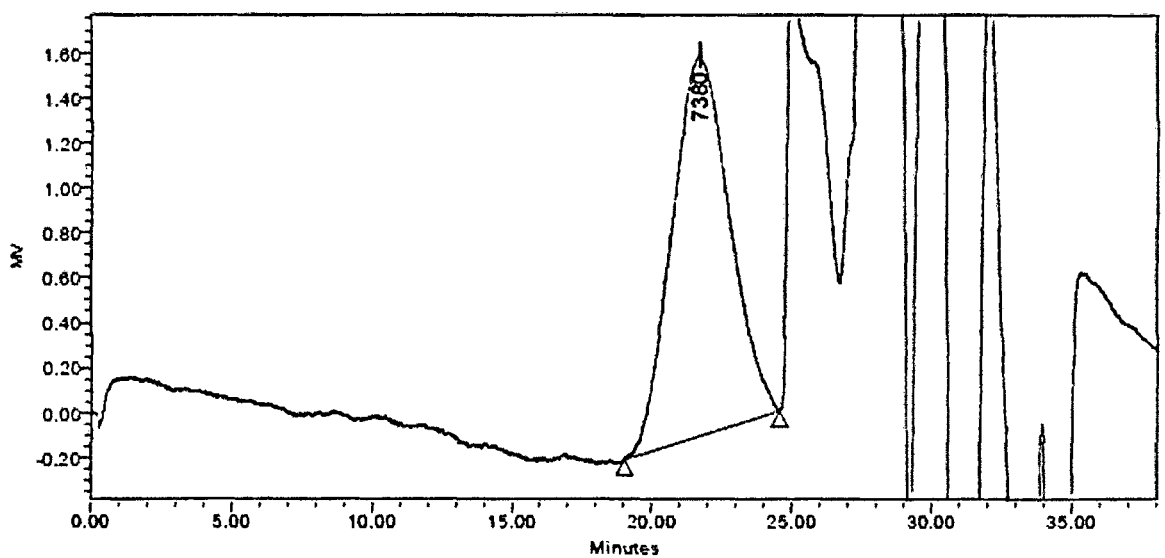
Figure 2:
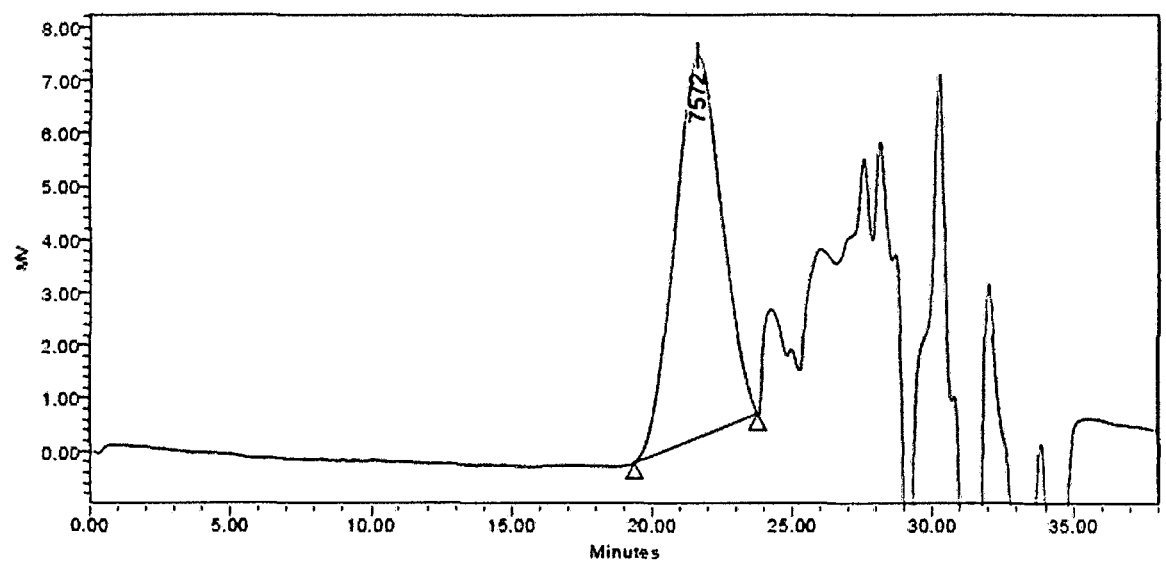
Figure 2:
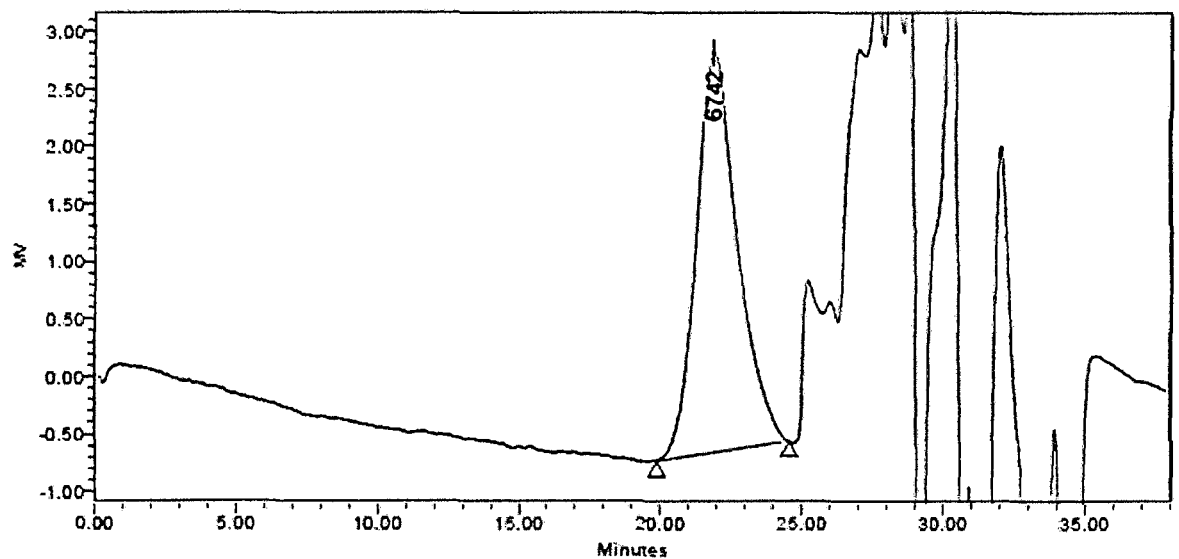

The terms "macroligand", "macromolecular monodentate ligand" and "macromolecular bidentate ligand" refer to a molecule of relatively high molecular weight (>1000 g/mol), natural or synthetic, having a linear or branched chain that contains a repeating unit, and having at least at one of its chain ends one or more functional groups allowing their coordination to metal center(s) and which can also have at one of its chain ends biomolecules or molecules of biological interest as hereinafter defined. The polymers, understood as including also copolymers or biopolymers, natural or synthetic, constituents of the macroligands are defined below.

By "monomer of interest" is meant any small molecule that can bind to other monomers forming larger molecules called (co)polymers.

The term "polymerization" that includes also the copolymerization(s) should be understood as the chemical reaction that gives rise to the (co)polymers.

"Polymer" refers to a molecule, natural or synthetic having in its structure a linear or branched chain, containing one or more repeating units called monomers. Preferred examples of polymers are, but without limitation, polylactide, polycaprolactone, poly-N-(2-hydroxypropyl)methacrylamide, poly(γ,L-glutamic acid), poly(citric acid), polyethylene glycol, polyaspartic acid, among others. In the description of the syntheses and in Formulae (I) to (IV) according to the invention, the term "polymer" comprises indistinctly also copolymers or biopolymers, natural or synthetic.

By "copolymer" is meant a polymer formed by different monomers. Preferred examples of copolymers include, but without limitation, poly(γ,L-glutamic acid)-citric acid, poly(ethylene glycol)-block-poly(glutamic acid), poly(ethylene glycol)-block-polyaspartic acid, poly(ethylene glycol)-poly(lactic acid), poly(ethylene glycol)-poly(caprolactone).

In the context of polymerization "catalyst" is a molecule that speeds up a chemical reaction, but is not itself consumed. The catalyst is part of the reaction but is regenerated at the end of each reaction cycle. Therefore, one catalyst unit results in the conversion of several reagent units. The catalyst must be distinguished from the "initiator". The initiator starts a chain of reactions, but is consumed in the reaction. It is not a catalyst. (IUPAC—Manual of Symbols and Terminology for Physicochemical Quantities and Units. Prepared for publication by Robert L. Burwell, Jr. Pergamon Press).

By "biopolymers", natural or synthetic, are meant polymers produced by living beings or polymers that mimic biopolymers obtained by chemical processes; preferred examples of biopolymers are, but without limitation, cellulose, starch, chitin, proteins, peptides, DNA and RNA.

By "biomolecule" is meant any chemical compound existing in living beings or a molecule that mimics a biomolecule, synthesized by chemical processes; preferred biomolecules are, but without limitation, amino acids, peptides, oligopeptides, proteins, protein fragments, estradiol and its derivatives, vitamins, carbohydrates, water, nucleic acids, among others. Some biomolecules due to its chemical structure that contains heteroaromatic atoms can themselves be understood as a "heteroaromatic ligand".

By "molecule of biological interest" is meant any natural or synthetic molecule with potential bioactivity. A compound is considered "bioactive" if it has an interaction or effect towards any cellular living tissue.

By "heteroaromatic ligand" is meant any molecule with a single ring or multiple ring system in which at least one of the rings has at least one heteroatom, such as N, O, S, Se, P, among others.

By "monodentate ligand" is meant any molecule having one atom with electronic availability to form coordination bonds to the transition metal; preferred monodentate ligands are, but without limitation, phosphanes, heteroaromatic molecules (which heteroatom can be O, S, P, N, Se, among others), CO, dimethyl sulfoxide, acetonitrile, nitriles, isonitriles, dimethylformamide, among others.

By "bidentate ligand" is meant any molecule having two atoms with electronic availability to form coordination bonds to the same metal center; preferred bidentate ligands are, but without limitation, diphosphanes, heteroaromatic molecules, oxalates, glycinate, trimethylethylenediamine, ethylenediamine, among others.

By metal salts ($MX_3$) are meant halide, nitrite, phosphate, perchlorate or carbonate salts represented by X, of any suitable transition metal represented by M, in particular ruthenium, iron, rhodium, iridium or osmium.

It was found that best results are obtained using as antitumoral agents the compounds of the present invention having the general structural Formula (I):

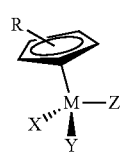
(I)

represented by the molecular formula [M(CpR)XYZ], wherein:
M is ruthenium, iron, rhodium, iridium or osmium;
CpR is cyclopentadienyl wherein R is H or substituted cyclopentadienyl, R being selected from: a biomolecule, a heteroaromatic ligand, a bioactive compound or a radical —$R_1$, —$R_1$—$NH_2$, —$R_1$—CCOH, —$R_1$—COO—, —$R_1$—COONCH$_3$, wherein R1 is an alkyl or aryl group; the R groups, can be bonded to the cyclopentadienyl ring at any of the ring carbons. R can occupy more than one carbon atom, can give rise to a cyclopentadienyl ring substituted in the positions 1, 2, 3, 4 and/or 5;
one of the X, Y or Z ligands is a macroligand, which can itself be a heteroaromatic ligand, X, Y and Z can be selected from heteroaromatic ligands, macroligands, CO, dimethyl sulfoxide, a biomolecule or a molecule of biological interest under the following conditions:
at least one of X, Y or Z is a heteroaromatic ligand, CO or dimethyl sulfoxide; and
at least one of the X, Y or Z ligands comprises or is a biomolecule or a molecule of biological interest;
and one of the following conditions:
X, Y and Z are any suitable monodentate ligands, preferably selected from phosphanes; heteroaromatic molecules wherein the heteroatom can be any suitable heteroatom, and is, preferably, selected from O, S, P, N or Se; CO; dimethyl sulfoxide; acetonitrile; nitriles; isonitriles; dimethylformamide; a biomolecule or a molecule of biological interest and at least one of X, Y or Z includes a macroligand; or
X and Y together represent any suitable bidentate macroligand preferably selected from macromolecular diphosphanes, macromolecular heteroaromatic molecules having at least one methyleneoxy or aminooxy function at the heteroaromatic ring(s), macromolecular oxalates or macromolecular glycinates and Z is any suitable monodentate ligand preferably selected from phosphanes, heteroaromatic molecules wherein the heteroatom can be any suitable heteroatom and is preferably selected from O, S, P, N or Se; CO; dimethyl sulfoxide; acetonitrile; nitriles; isonitriles; or dimethylformamide;
X and Y together represent any suitable bidentate ligand preferably selected from diphosphanes, heteroaromatic molecules, oxalates, glycinates, trimethylethylenediamine, ethylenediamine, a biomolecule or a molecule of biological interest, and Z is any suitable monodentate ligand preferably selected from macromolecular phosphanes, macromolecular heteroaromatic molecules wherein the heteroatom can be any suitable heteroatom and is preferably selected from O, S, P, N or Se; macromolecular nitriles; or macromolecular isonitriles.

Thus, in one aspect of the present invention a group of especially preferred compounds of formula (I) is that represented by the general formula (II):

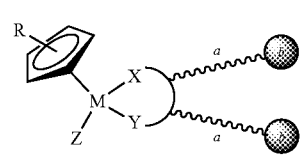
Formula (II)

wherein
R is H;
M represents ruthenium or iron;
X and Y together represent a bidentate macroligand having at least one methyleneoxy or aminooxy function at the heteroaromatic ring(s), which can contain, preferably, at its chain end one or more molecules of biological interest or a biomolecule;

Z represents phosphane, CO, dimethyl sulfoxide, a heteroaromatic monodentate ligand, a molecule of biological interest or a ligand including a molecule of biological interest or biomolecule;
a represents polymer; and
b represents a molecule of biological interest.

Another group of especially preferred compounds of formula (I) is that represented by the general formula (III):

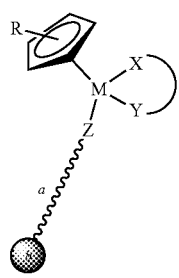

(III)

wherein
R is H;
M represents ruthenium or iron;
X and Y together represent a bidentate heteroaromatic ligand or a molecule of biological interest or biomolecule;
Z represents a macromolecular monodentate phosphane ligand, which can contain at its chain end a molecule of biological interest or a biomolecule;
a represents a polymer; and
b represents a molecule of biological interest.

Another group of especially preferred compounds of formula (I) is that represented by the general formula (IV):

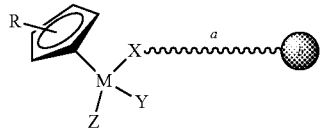

(IV)

wherein
R is H;
M represents ruthenium or iron;
Z represents a monodentate macroligand, wherein the polymer is preferably bonded to a phosphane or a heteroaromatic ligand, which can contain at its chain end a molecule of biological interest;
Y preferably represents CO;
X represents a halide, a ligand of biological interest or a biomolecule;
a represents a polymer; and
b represents a molecule of biological interest or a biomolecule.

The compounds of formula (I) can be cationic or neutral and can be in salt form whose anions can be, for example, halides, phosphates, triflates, phenylborates, hexafluorophosphates, among others.

Especially preferred compounds according to the present invention are the following:

(2,2'-bipyridine-4,4'-diylbis{methylene}bis(2-{2-(2-hydroxypropanoyloxy)poly(lactic acid)-yl}propanoate)-k²N,N')(carbonyl)η⁵-cyclopentadienyl)ruthenium(II) hexafluorophosphate (Compound 1) of formula (V):

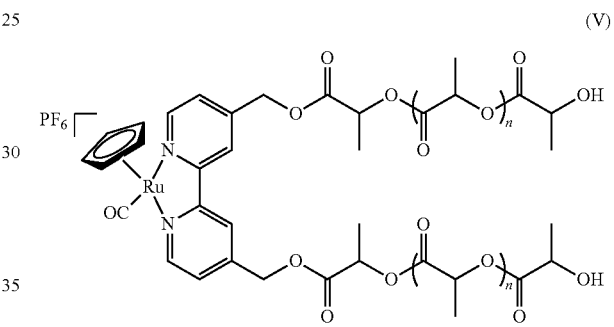

(V)

[(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dianthracene-9-carboxylate)-k²N,N'](carbonyl)(η⁵-cyclopentadienyl)ruthenium(II) hexafluorophosphate—(Compound 2) of formula (VI):

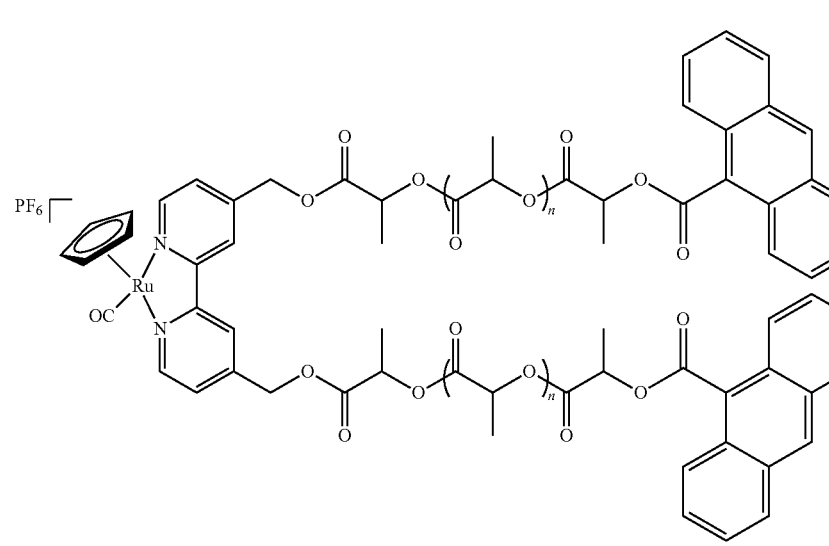

(VI)

[1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dianthracene-9-carboxylate)-k²N,N'](triphenylphosphane)(η⁵-cyclopentadienyl)ruthenium(II))triflate (Compound 3) of formula (VII):

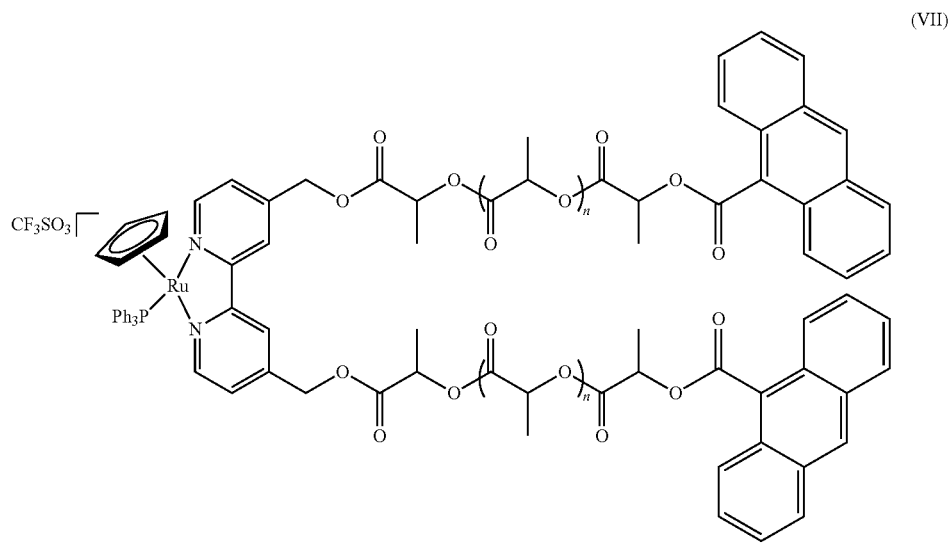

(VII)

[(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dinaphthalene-2-carboxylate)-k²N,N'](triphenylphosphane)(η⁵-cyclopentadienyl)ruthenium(II) triflate (Compound 4) of formula (VIII):

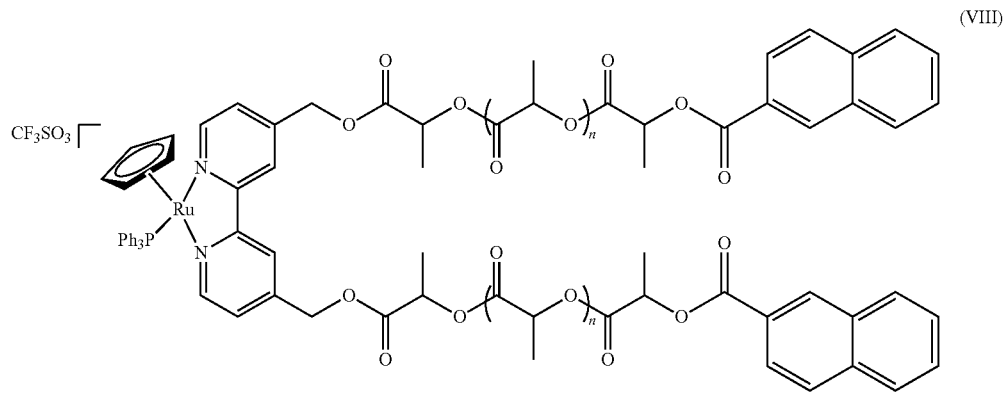

(VIII)

(2,2'-bipyridine-4,4'-diylbis{methylene}bis(2-{2-(2-hydroxypropanoyloxy)poly(lactic acid)-yl}propanoate)-k²N,N')(triphenylphosphane)(η⁵-cyclopentadienyl)ruthenium(II) triflate (Compound 5) of formula (IX):

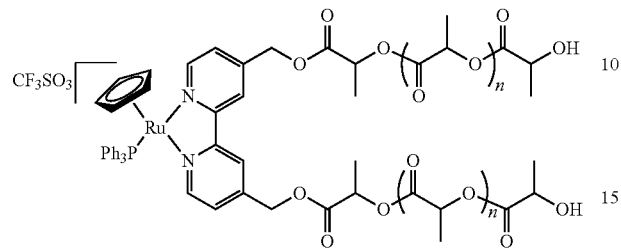

[(1,1'-{1,1'-(1,1'-{2,2'-Bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)di(2S,3S,4S,5R,6R)-3,4,5,6-tetrahydroxyoxane-2-carboxylate)-k²N,N'](triphenylphosphane)(η⁵-cyclopentadienyl)-ruthenium(II) triflate (Compound 6) of formula (X):

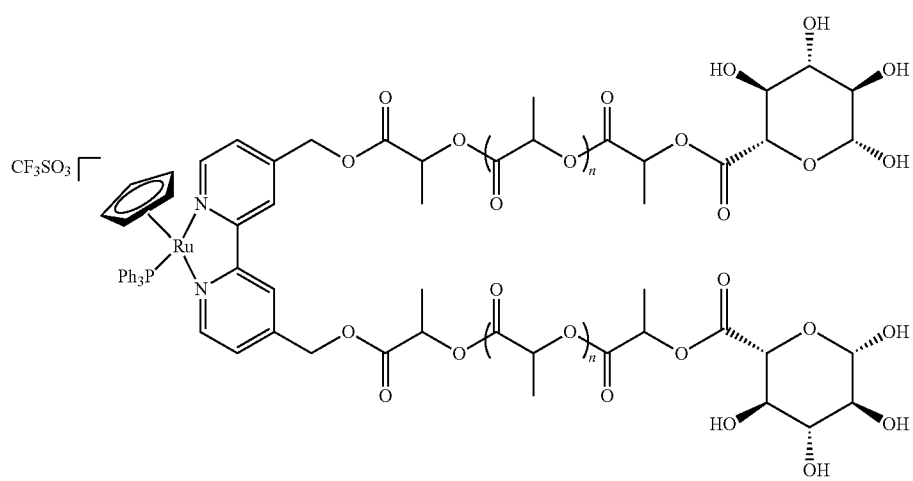

[1-({1-({1-(Benzyloxy)-1-oxopropane-2-yl})oxy)-1-(poly(lactic acid)))}-1-oxopropane-2-yl-4-(diphenylphosphino)benzoate-k¹P]carbonyl)(iodide)(η⁵-cyclopentadienyl)iron(II) (Compound 7) of formula (XI):

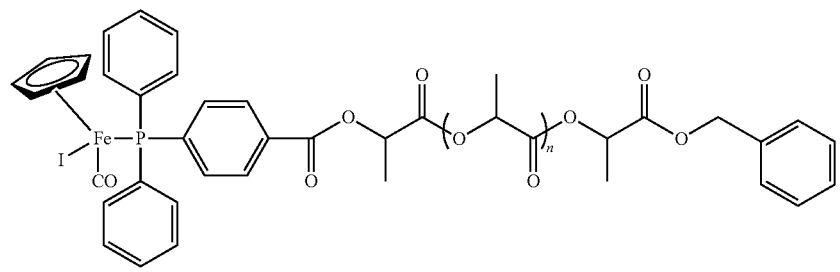

[Tris(1-{1-(1-hydroxypropanoyloxy)poly(lactic acid)-yl}propanoate)phosphane-k¹P](carbonyl)-(iodide)(η⁵-cyclopentadieny)iron(II) (Compound 8) of formula (XII):

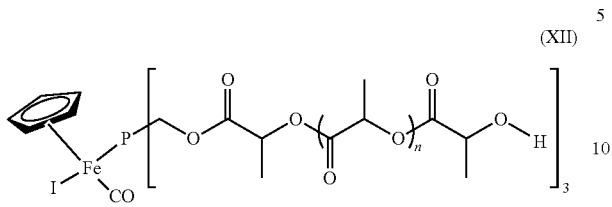

(XII)

[(1-({1-({1-(Benzyloxy)-1-oxopropane-2-yl}oxy)-1-(poly-(lactic acid))}-1-oxopropane-2-yl)-4-(diphenylphosphino)benzoate-k¹P]((2-benzoylpyridine)-k²N,O)(η⁵-cyclopentadienyl) ruthenium(II) triflate—(Compound 9) of formula (XIII):

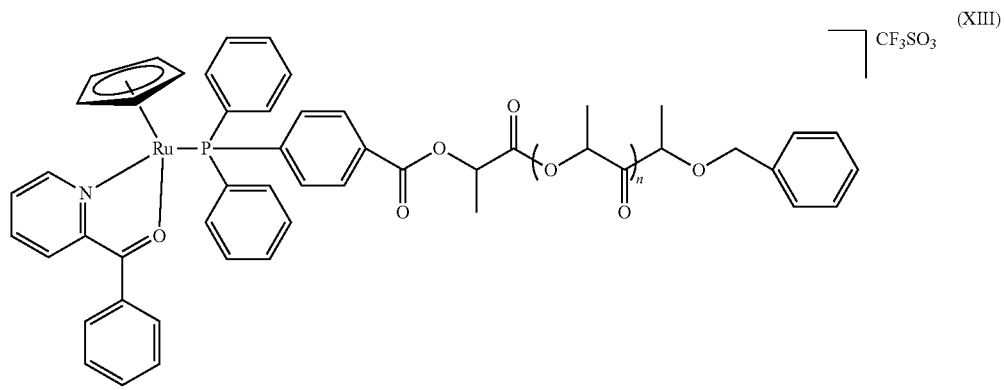

(XIII)

The present invention refers to bidentate macroligands of general formula (XIV):

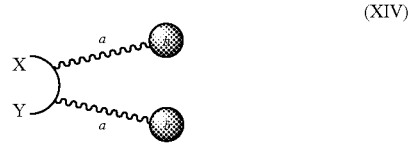

(XIV)

wherein
X and Y together represent a macromolecular bidentate phosphane ligand or a macromolecular bidentate heteroaromatic ligand having at least one methyleneoxy or aminooxy function at the heteroaromatic ring(s), and it can contain, preferably, at its chain end one or more molecules of biological interest or a biomolecule;
a represents a polymer;
b represents a molecule of biological interest or a biomolecule.

The present invention also refers to monodentate macroligands of general formula (XV):

(XV)

wherein
Z represents a macromolecular heteroaromatic monodentate ligand or a macromolecular monodentate phosphane and it can contain at its chain end one or more molecules of biological interest or a biomolecule;
a represents polymer;
b represents a molecule of biological interest or a biomolecule.

Preferred macromolecular bidentate heteroaromatic ligands of the present invention are as follows:
a) 1,1'-{1,1'-(1,1'-{2,2'-bipyridine-4,4'-di-ylbis(methylene)}bis(oxy)bis(1-oxopropane-2,1-di-yl))-bis(poly(lactic acid)-yl))}bis(oxy)bis(1-oxopropane-2,1-di-yl)dianthracene-9-carboxylate of formula (XVI):

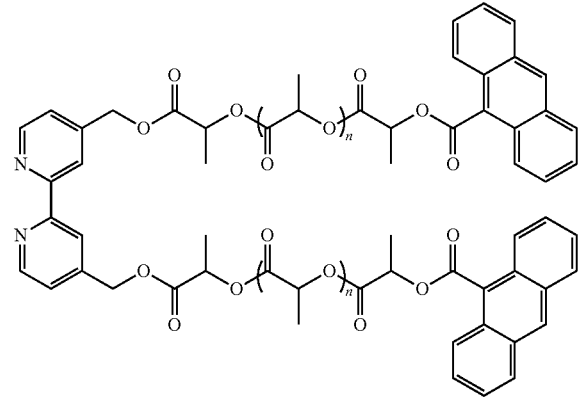

(XVI)

b) 1,1'-{1,1'-(1,1'-{2,2'-bipyridine-4,4'-di-ylbis(methylene)}bis(oxy)bis(1-oxopropane-2,1-di-yl))bis(poly(lactic acid)-yl))}bis(oxy)bis(1-oxopropane-2,1-di-yl)dinaphthalene-2-carboxylate of formula (XVII):

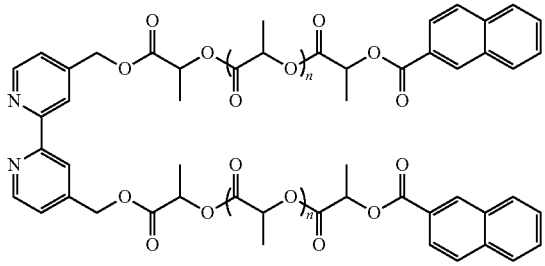

c) 1,1'-{1,1'-(1,1'-{2,2'-bipyridine-4,4'-di-ylbis(methylene)}bis(oxy)bis(1-oxopropane-2,1-di-yl))bis(poly(lactic acid)-yl))}bis(oxy)bis(1-oxopropane-2,1-di-yl)di(2S,3S,4S,5R,6R)-3,4,5,6-tetra-hydroxyoxane-2-carboxylate of formula (XVIII):

(XVIII)

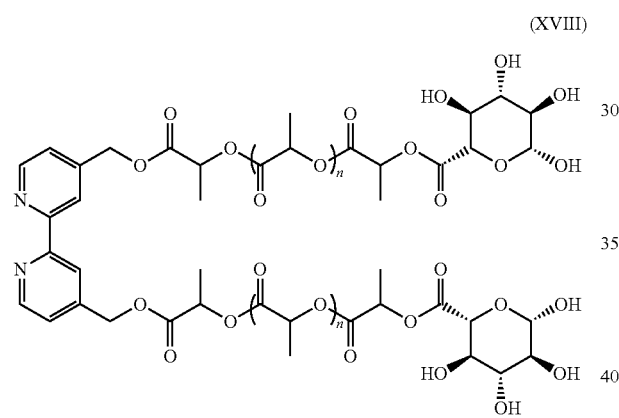

Preferred macromolecular monodentate phosphane ligands of the present invention are as follows:

d) 1-({1-({1-(benzyloxy)-1-oxopropane-2-yl}oxy)-1-(poly-(lactic acid))}-1-oxopropane-2-yl 4-(diphenylphosphino)benzoate of formula (XIX):

(XIX)

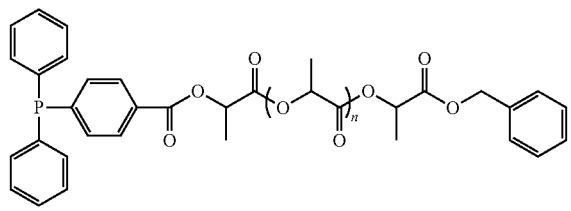

e) tris(1-{1-(1-hydroxypropanoyloxy)poly(lactic acid)-yl}propanoato)phosphane of formula (XX):

(XX)

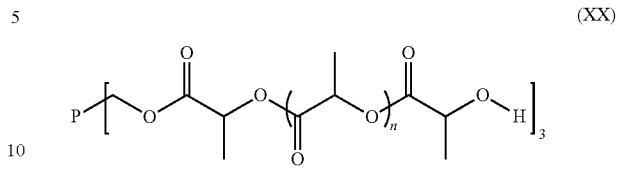

In another aspect, it is an object of the present invention to provide a synthetic procedure for the new organometallic compounds.

Step 1) Synthesis of Macroligands a) Synthesis of Heteroaromatic Macroligands

The synthesis of heteroaromatic macroligands can be carried out as follows:

i) A heteroaromatic ligand, selected from pyridines, bipyridines, imidazoles, among others, containing, for example, a primary amine or alcohol function, acts as initiator and/or catalyst of polymerization of the monomer(s) of interest, to provide the heteroaromatic macroligand. The heteroaromatic macroligand obtained can be purified, if necessary, by the usual purification techniques and bonded to a molecule of biological interest (e.g. sugars, estrogen, molecules that contain conjugated it systems, among others) by reactions of condensation, substitution, addition, elimination, redox, rearrangement or pericyclic reaction.

ii) A previously prepared or commercially available polymer is reacted by reactions of condensation, substitution, addition, elimination, redox, rearrangement or pericyclic reaction with a heteroaromatic ligand (e.g. pyridines, bipyridines, and imidazoles, among others). The heteroaromatic macroligand obtained can be purified, if necessary, by the usual purification techniques and bonded to a molecule of biological interest (e.g. sugars, estrogen, molecules that contain conjugated π systems, N-(3-{[5-(4-chlorophenyl)-1H-pirrolo[2,3-b]pyridine-3-yl]carbonyl}-2,4-difluorophenyl)propane-1-sulfonamide, bromocriptine, 4-methyl-5-oxo-2,3,4,6,8-pentaazabicyclo[4.3.0]nona-2,7,9-trieno-9-carboxamide, among others), by reactions of condensation substitution, addition, elimination, redox, rearrangement or pericyclic reaction.

iii) A molecule of biological interest (e.g. amino acids, DNA bases, among others) containing, for example, a primary amine or alcohol function, serve as initiator and/or catalyst to the polymerization of the monomer(s) of interest. The macromolecule obtained can be purified, if necessary, by the usual purification techniques and bonded to heteroaromatic ligand (e.g. pyridines, bipyridines, imidazoles, among others) by reactions of condensation, substitution, addition, elimination, redox, rearrangement or pericyclic reaction, to provide the heteroaromatic macroligand.

iv) A previously prepared or commercially available polymer is reacted by reactions of condensation, substitution, addition, elimination, redox, rearrangement or pericyclic reaction with a molecule of biological interest (e.g. sugars, estrogen, molecules that contain conjugated π systems, N-(3-{[5-(4-chlorophenyl)-1H-pirrolo[2,3-b]pyridine-3-yl]carbonyl}-2,4-difluorophenyl)propane-1-sulfonamide, bromocriptine, 4-methyl-5-oxo-2,3,4,6,8-pentazabicyclo[4.3.0]nona-2,7,9-trieno-9-carboxamide among others). This macromolecule can be purified, if necessary, by the usual purification techniques and bonded to heteroaromatic (e.g. pyridines, bipyridines, and imidazoles, among others) ligand by reactions of condensation, substitution, addition, elimination, redox, rearrangement or pericyclic reaction, to provide the heteroaromatic macroligand.

b) Synthesis of Macromolecular Phosphanes

The synthesis of macromolecular phosphanes can be carried out as follows:

i) A phosphane containing, for example, a primary amine or alcohol function, serves as initiator and/or catalyst to the polymerization of the monomer(s) of interest, to provide the macromolecular phosphane. The macromolecular phosphane obtained can be purified, if necessary, by the usual purification techniques and bonded to a molecule of biological interest (e.g. sugars, estrogen, molecules that contain conjugated it systems, N-(3-{[5-(4-clorophenyl)-1H-pirrolo[2,3-b]pyridine-3-yl]carbonyl}-2,4-difluorophenyl)propane-1-sulfonamide, bromocriptine, 4-methyl-5-oxo-2,3,4,6,8-pentazabicyclo[4.3.0]nona-2,7,9-trieno-9-carboxamide among others) by reactions of condensation, substitution, addition, elimination, redox, rearrangement or pericyclic reaction.

ii) A phosphane is reacted with a previously prepared or commercially available polymer, by reactions of condensation, substitution, addition, elimination, redox, rearrangement or pericyclic reaction to provide a macromolecular phosphane. After purification, if necessary, by the usual purification techniques, the macromolecular phosphane can be bonded to a molecule of biological interest (e.g. sugars, estrogen, molecules that contain conjugated it systems, among others) by reactions of condensation, substitution, addition, elimination, redox, rearrangement or pericyclic reaction.

iii) A molecule of biological interest (e.g. sugars, estrogen, molecules that contain conjugated $\pi$ systems, among others) containing, for example, a primary amine or alcohol function, serves as initiator and/or catalyst to the polymerization of the monomer(s) of interest, to provide the macroligand. This macromolecule can be purified, if necessary, by the usual purification techniques and bonded to a phosphane by reactions of condensation, substitution, addition, elimination, redox, rearrangement or pericyclic reaction, to provide the macromolecular phosphane.

iv) A previously prepared or commercially available polymer, is reacted, by reactions of condensation, substitution, addition, elimination, redox, rearrangement or pericyclic reaction, with a molecule of biological interest (e.g. sugars, estrogen, molecules that contain conjugated $\pi$ systems, N-(3-{[5-(4-clorophenyl)-1H-pirrolo[2,3-b]pyridine-3-yl]carbonyl}-2,4-difluorophenyl)propane-1-sulfonamide, bromocriptine, 4-methyl-5-oxo-2,3,4,6,8-pentazabicyclo[4.3.0]nona-2,7,9-trieno-9-carboxamide, among others). This macromolecule can be purified, if necessary, by the usual purification techniques and bonded to a phosphane by reactions of condensation, substitution, addition, elimination, redox, rearrangement or pericyclic reaction, to provide the macromolecular phosphane.

Step 2) Synthesis of the Macromolecular Organometallic Complexes of Transition Metals i) For the synthesis of complexes of the present invention of general formula (I) wherein X and Y represent two macromolecular monodentate phosphane ligands, and Z is a heteroaromatic monodentate ligand, CO, dimethyl sulfoxide, a biomolecule or a molecule of biological interest; or X and Y together represent a macromolecular bidentate phosphane ligand; Z is a heteroaromatic monodentate ligand, CO, dimethyl sulfoxide, a biomolecule or a molecule of biological interest; or X is a macromolecular monodentate phosphane ligand, and Y and Z together represent a bidentate heteroaromatic ligand, a biomolecule or a molecule of biological interest, reaction between compound of formula [M(CpR)(PP)L] wherein PP represents two macromolecular monodentate phosphane ligands or a macromolecular bidentate phosphane ligand, L is a halide, such as for example chloride or iodide, and a heteroaromatic mono or bidentate ligand L1, CO, dimethyl sulfoxide, a biomolecule or a molecule of biological interest.

ii) For the synthesis of complexes of the present invention of general Formula (I) wherein X and Y represent two monodentate phosphane ligands, Z is a macromolecular monodentate heteroaromatic ligand; or X and Y together represent a bidentate phosphane ligand, Z is a macromolecular monodentate heteroaromatic ligand; or X is a monodentate phosphane ligand; Y and Z together represent a macromolecular bidentate heteroaromatic ligand having at least one methyleneoxy or aminooxy function at the heteroaromatic ring(s), reaction between macromolecular heteroaromatic ligand and a complex [M(CpR)(PP)L] wherein PP represents two monodentate phosphane ligands or a bidentate phosphane ligand; L is a halide, such as for example chloride or iodide.

iii) For the synthesis of complexes of the present invention of general Formula (I) wherein X and Y represent two macromolecular monodentate phosphane ligands, Z is a heteroaromatic monodentate ligand, CO, dimethyl sulfoxide, a biomolecule or a molecule of biological interest; or X and Y together represent a macromolecular bidentate phosphane ligand, Z is a heteroaromatic monodentate ligand, CO, dimethyl sulfoxide, a biomolecule or a molecule of biological interest; or X is a macromolecular monodentate phosphane ligand; Y and Z together represent a bidentate heteroaromatic ligand, a biomolecule or a molecule of biological interest, direct reaction between metal salt ($MX_3$), hydrated or not hydrated, and a cyclopentadienyl derivative (CpR) and an excess of the macromolecular phosphane. Purification of the compound of general Formula [M(CpR)(PP)L] obtained (wherein PP represents two macromolecular monodentate phosphane ligands or a macromolecular bidentate phosphane ligand; L is a halide, such as for example chloride or iodide) is followed by a reaction of substitution of the halide (and eventually of one macromolecular phosphane) by a heteroaromatic mono or bidentate ligand, CO, dimethyl sulfoxide, a biomolecule or a molecule of biological interest, to provide a final compound of the Formula [M(CpR)XYZ].

iv) For the synthesis of complexes of the present invention of general Formula (I) wherein X and Y represent two macromolecular monodentate phosphane ligands, Z is a heteroaromatic monodentate ligand, CO, dimethyl sulfoxide, a biomolecule or a molecule of biological interest; or X and Y together represent a macromolecular bidentate phosphane ligand, Z is a heteroaromatic monodentate ligand, CO, dimethyl sulfoxide, a biomolecule or a molecule of biological interest; or X is a macromolecular monodentate phosphane ligand; Y and Z together represent a bidentate heteroaromatic ligand, a biomolecule or a molecule of biological interest, direct reaction between metal salt ($MX_3$), hydrated or not hydrated, and a cyclopentadienyl derivative (CpR) and an excess of phosphane that contains a functional group allowing a further functionalization, such as for example the carboxyl group. Purification of the compound of general Formula [M(CpR)(PP)L] obtained (wherein PP represents two monodentate phosphane ligands that contains a functional group or a bidentate phosphane ligand that contains a functional group; L is a halide, such as for example chloride or iodide), is followed by a reaction of substitution of the halide (and eventually of one phosphane that contains a functional group) by a heteroaromatic mono or bidentate ligand, CO, dimethyl sulfoxide, a biomolecule or a molecule of biological interest. Then, the compound obtained is reacted with a previously prepared or commercially available polymer, by reactions of condensation, substitution, addition, elimination, redox, rearrangement or pericyclic reaction, to provide a final compound of the Formula [M(CpR)XYZ].

v) For the synthesis of complexes of the present invention of general Formula (I) wherein X and Y represent two macromolecular monodentate phosphane ligands, Z is a heteroaromatic monodentate ligand, CO, dimethyl sulfoxide, a biomolecule or a molecule of biological interest; or X and Y together represent one macromolecular bidentate phosphane ligand, Z is a heteroaromatic monodentate ligand, CO, dimethyl sulfoxide, a biomolecule or a molecule of biological interest; or X is a macromolecular monodentate phosphane ligand; Y and Z together represent a bidentate heteroaromatic ligand, a biomolecule or a molecule of biological interest; or X and Y represent two monodentate phosphane ligands, Z is a macromolecular monodentate heteroaromatic ligand; or X and Y together represent a bidentate phosphane ligand, Z is a macromolecular monodentate heteroaromatic ligand; or X is a monodentate phosphane ligand; Y and Z together represent a macromolecular bidentate heteroaromatic ligand having at least one methyleneoxy or aminooxy function at the heteroaromatic ring(s), reaction between macromolecular ligand and a complex [M(CpR)(NCMe)$_3$]$^+$[W]$^-$ with substitution of 1 or 2 acetonitriles according to the options given above. Then, without isolating this compound, reacting with the other ligand(s) of interest (heteroaromatic mono or bidentate ligand, mono or bidentate phosphane, a biomolecule or a molecule of biological interest), to provide the compound of the desired Formula [M(CpR)XYZ]$^+$[W]$^-$ (wherein W is an anion preferably selected from PF$_6$, CF$_3$SO$_3$, Cl, I, BPh$_4$, among others).

vi) For the synthesis of complexes of the present invention of general Formula (I) wherein X and Y represent two macromolecular monodentate phosphane ligands, Z is a heteroaromatic monodentate ligand, CO, dimethyl sulfoxide, a biomolecule or a molecule of biological interest; or X is a macromolecular monodentate phosphane ligand, Y and Z represent monodentate heteroaromatic ligands, CO, dimethyl sulfoxide, biomolecule or molecule of biological interest reaction between the metal salt ($MX_3$), hydrated or not hydrated, X is a halide such as for example chloride or iodide, and a macromolecular phosphane in excess, to provide the compound [Ru(macromolecular phosphane)$_3$L$_n$] (n is 2 or 3). Thereafter, this compound is reacted with (CpR)Na, or (CpR) in the presence of KOBut, to provide the compound [M(CpR)(PP)L] (PP represents two macromolecular monodentate phosphane ligands). Following isolation, L (and eventually one macromolecular phosphane) is(are) substituted(s) by mono or bidentate heteroaromatic ligand(s), CO, dimethyl sulfoxide, a biomolecule or a molecule of biological interest to provide a final compound of the Formula [M(CpR)XYZ].

vii) For the synthesis of complexes of the present invention of general Formula (I) wherein X and Y together represent a macromolecular bidentate phosphane ligand, Z is a heteroaromatic monodentate ligand, CO, dimethyl sulfoxide, a biomolecule or a molecule of biological interest reaction between [Ru(PPh$_3$)$_3$Cl$_n$] wherein n is 2 or 3 and a macromolecular bidentate phosphane to provide the compound [Ru(macromolecular bidentate phosphane)$_2$Cl$_n$] (n is 2 or 3). Thereafter, this compound is reacted with (CpR)Na, or (CpR) in the presence of KOBut, to provide the compound [M(CpR)(PP)L] (PP is macromolecular bidentate phosphane; L is a halide). Following isolation, L is substituted by a heteroaromatic monodentate ligand, CO, dimethyl sulfoxide, a biomolecule or a molecule of biological interest to provide a final compound of the Formula [M(CpR)XYZ].

viii) For the synthesis of complexes of the present invention of general Formula (I) wherein X and Y represent two macromolecular monodentate phosphane ligands, Z is a heteroaromatic monodentate ligand, CO, halide, dimethyl sulfoxide, biomolecule or molecule of biological interest; or X is a macromolecular monodentate phosphane ligand, Y and Z represent monodentate heteroaromatic ligands, CO, a halide, dimethyl sulfoxide, biomolecule or a molecule of biological interest reaction between [M(CpR)(CO)$_2$L] wherein L is a halide, such as for example chloride or iodide, and a macromolecular phosphane to provide a complex of the type [M(CpR)X(CO)L] wherein X is a macromolecular monodentate phosphane, L is a halide. One or both of CO and L can be substituted by a heteroaromatic monodentate ligand, CO, a halide, dimethyl sulfoxide, a biomolecule or a molecule of biological interest, to provide a final compound of the Formula [M(CpR)XYZ].

ix) For the synthesis of complexes of the present invention of general Formula (I) wherein X and Y together represent a macromolecular bidentate phosphane ligand, Z is a heteroaromatic monodentate ligand, CO, a halide, dimethyl sulfoxide, a biomolecule or a molecule of biological interest, reaction between [M(CpR)(CO)$_2$L] wherein L is a halide, and a macromolecular bidentate phosphane to provide a compound of formula [M(CpR)XYL] wherein X and Y together represent a macromolecular bidentate phosphane ligand and L is a halide). L is then substituted by a heteroaromatic monodentate ligand, CO, dimethyl sulfoxide, a biomolecule or a molecule of biological interest.

These compounds, having the same general structure, and the same '1\4(CpR)' fragment allows for a very critical synthesis of the polymers and molecules of biological interest very focused on the intended purpose, as the syntheses performed have a high yield (70-90%) and, in most cases, without the need for additional purifications. The products are obtained with a purity degree of between 80-95%, suitable for use as pharmaceuticals, as can be seen by the monomodal character of the chromatograms obtained by gel permeation chromatography (FIGS. 2a to 2f) and by the values of dispersity of 1.1-1.4 (also calculated from the same chromatograms). The nuclear magnetic resonance allows the calculation of the percentage of functionalization that is between 80-95% as already mentioned.

The reactional medium for all the above described inorganic/organometallic syntheses comprises a solvent or a mixture of solvents selected from water, ethanol, methanol, ethyl acetate, isopropanol, tert-butanol, ethylene glycol, dimethylglyoxime, diethyl ether, chloroform, dichloromethane, benzene, toluene, acetone, tetrahydrofuran, dimethyl sulfoxide, dioxane, dimethylformamide or acetonitrile.

The procedures described above can occur at temperatures between −80° C. and 300° C., and at a pressure of $10^{-3}$ to 100 atm, with or without stirring, with irradiation by UV light if necessary, and with the addition of a salt where necessary.

The complexes of the present invention are air stable and stable in aqueous media for a period appropriate for medicinal purposes and have very relevant antitumor and antimetastatic properties.

Therefore, in another aspect, it is an object of the present invention to provide pharmaceutical compositions and medicaments comprising a pharmaceutically effective amount of at least one macromolecular complex of a transition metal of the present invention or a salt thereof, optionally in combination with other active ingredients and/or pharmaceutically acceptable vehicles and/or excipients.

The macromolecular organometallic complexes of transition metals de formula (I), (II), (III) or (IV) as defined above and the compositions and medicines in accordance with the invention can be used as medicaments for example in the treatment of tumors, both of the primary tumor and of the metastases it originated. Examples of tumors are breast, ovarian, prostate, pancreas carcinomas, glioma, leukaemia and melanoma, among others. They can also be used in photodynamic therapy for treating superficial cancers as cancer of the skin and pharynx, among others.

In yet another aspect, it is an object of the present invention the use of the compounds of formula (I) in medicament, namely in the cancer treatment and/or prevention, including the treatment of solid tumors, liquid tumors and/or metastases. Additionally, the compounds of the present invention can be used in pharmaceutical compositions or medicaments as antitumor agents and/or as radiosensitizer agents for cancer therapy.

The particular examples presented below are intended only to illustrate the present invent invention and should not be construed as limitation of the present invention.

DESCRIPTION OF EMBODIMENTS

Examples

I—Synthesis

Example 1

Synthesis of a heteroaromatic macroligand: 2,2'-bipyridine-4,4'-diylbis{methylene}bis(2-{2-(2-hydroxypropanoyloxy)poly(lactic acid)-yl}propanoate)

The synthesis was carried out using Schlenk techniques under nitrogen inert atmosphere and the solvents were previously dried and distilled under nitrogen atmosphere. A mixture of 1 g of 3,6-dimethyl-1,4-dioxane-2,5-dione, 56.5 mg of dimethylaminopyridine and 37.5 mg of 2,2'-bipyridine-4,4'-dimethanol was heated at 135° C. in an oil bath under stirring. After melting of the 3,6-dimethyl-1,4-dioxane-2,5-dione, it was allowed to stay for 5 minutes and after this period the reaction was quenched with the addition of an excess of a methanol/water mixture. Then, the product was precipitated in about 50 ml of a methanol/water mixture. The solvent was evaporated in vacuum and the product obtained was washed with diethyl ether and dried under vacuum to provide about 750 mg of the title compound as a white product.

$^1$H NMR [CDCl$_3$, Me$_4$Si, δ/ppm (multiplicity, assignment)]: 8.67 [d, H$_{meta}$ bipyridine], 8.30 [s, H$_{ortho}$ bipyridine], 7.27 H$_{para}$ bipyridine], 5.26 [s, —CH$_2$O bipyridine], 5.16 [m, —CH— polylactide main chain], 4.36 [q, —CH— polylactide end group], 1.55 [m, —CH$_3$ polylactide main chain], 1.49 [m, —CH$_3$ polylactide end group].

Example 2

Synthesis of a Heteroaromatic Macroligand Functionalized with a Molecule of Biological Interest: 1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl) dianthracene-9-carboxylate The synthesis was carried out using Schlenk techniques under nitrogen inert atmosphere and the solvents were previously dried and distilled under nitrogen atmosphere. 300 mg of the 2,2'-bipyridine-4,4'-diylbis{methylene}bis(2-{2-(2-hydroxypropanoyloxy)poly(lactic acid)-yl}-propanoate) obtained in example 1 were dissolved in anhydrous tetrahydrofuran (THF) and 25 μl of triethylamine added. The reaction continued for 1 h. After this period 36.5 mg of anthracene-9-carboxylic acid were added to the solution and the reaction continued at the THF reflux temperature until complete removal of the water formed during the reaction using a Dean-Stark apparatus. Finally the compound obtained was dried under vacuum to provide about 300 mg of the title compound 1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl) dianthracene-9-carboxylate as a white product.

¹H NMR [CDCl₃, Me₄Si, δ/ppm (multiplicity, assignment)]: 8.67 [d, $H_{meta}$ bipyridine], 8.38 [d, $H_{para}$ anthracene+$H_{ortho}$ bipyridine], 8.16 [d, H-aromatic anthracene], 7.95 [d, H-aromatic anthracene], 7.43 [t, H-aromatic anthracene], 7.27 [d, $H_{para}$ bipyridine], 5.26 [s, —CH₂O bipyridine], 5.16 [m, —CH— polylactide main chain], 4.36 [q, —CH— polylactide end group], 1.57 [m, —CH₃ polylactide main chain], 1.50 [m, —CH₃ polylactide end group].

Example 3

Alternative Synthesis of an Organometallic Complex of Ruthenium that Contains a heteroaromatic macroligand: (2,2'-bipyridine-4,4'-diylbis{methylene}bis(2-{2-(2-hydroxypropanoyloxy)poly(lactic acid)-yl}propanoate)-k²N,N')(carbonyl)($\eta^5$-cyclopentadienyl) ruthenium(II) hexafluorophosphate—Compound 1

The synthesis was carried out using Schlenk techniques under nitrogen inert atmosphere and the solvents were previously dried and distilled under nitrogen atmosphere. 15 mg of [Ru(Cp)(NCMe)₃][PF₆] were dissolved in anhydrous dichloromethane. The solution obtained was cooled to 0° C. using ice. Once the temperature of 0° C. is reached, 170 mg of the 2,2'-bipyridine-4,4'-diylbis {methylene}bis(2-{2-(2-hydroxypropanoyloxy)poly(lactic acid)-yl}propanoate) obtained in example 1 were added. After 5 min, the solution was removed from the ice and left to react for about 30 min at room temperature. After this time, a CO flow was passed through for about 15 min. Then, the solution was filtered with Celite and the filtrate was evaporated to the compound precipitation limit. About 15 ml of anhydrous hexane was added to force precipitation. The solution was decanted and the precipitate was dried under vacuum. The product was recrystallized from anhydrous dichloromethane/hexane to provide 150 mg of the title compound (2,2'-bipyridine-4,4'-diylbis{methylene}bis(2-{2-(2-hydroxypropanoyloxy)poly(lactic acid)-yl}-propanoate)-k²N,N')(carbonyl)($\eta^5$-ciclopenta-dienilo)ruthenium(II) hexafluorophosphate as a brownish salt.

¹H NMR [acetone-d6, Me₄Si, δ/ppm (multiplicity, assignment)]: 9.28 [d, $H_{meta}$ bipyridine], 8.49 [s, $H_{ortho}$ bipyridine], 7.69 [$H_{para}$ bipyridine], 5.51 [s, $\eta^5$-cyclopentadienyl], 5.30 [m, —CH— polylactide main chain+-CH₂O bipyridine], [q, —CH— polylactide end group], 1.55 [m, —CH₃ polylactide main chain], 1.39 [m, —CH₃ polylactide end group].

Example 4

Alternative Synthesis of an Organometallic Complex of Ruthenium that Contains a Heteroaromatic Macroligand: [(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dianthracene-9-carboxylate)-k²N,N'](carbonyl)($\eta^5$-cyclopentadienyl) ruthenium(II) hexafluorophosphate—Compound 2

The synthesis was carried out using Schlenk techniques under nitrogen inert atmosphere and the solvents were previously dried and distilled under nitrogen atmosphere. 15 mg of [Ru(Cp)(NCMe)₃][PF₆] were dissolved in anhydrous dichloromethane. The solution obtained was cooled to 0° C. using ice. Once the temperature of 0° C. is reached, 170 mg of the 1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dianthracene-9-carboxylate obtained in example 2 were added. After 5 min, the solution was removed from the ice and left to react for about 30 min at room temperature. After this time, a CO flow was passed through for about 15 min. Then, the solution was filtered with Celite and the filtrate was evaporated to the compound precipitation limit. About 15 ml of anhydrous hexane was added to force precipitation. The solution was decanted and the precipitate was dried under vacuum. The product was recrystallized from anhydrous dichloromethane/hexane to provide about 150 mg of the compound [(1,1'-{1,1'-(1,1'-{2,2'-bipyridine-4,4'-diylbis(methylene)}bis(oxy)bis(1-oxopropane-2,1-diyl))bis-(poly(lactic acid)-yl))}bis(oxy)bis(1-oxopropane-2,1-diyl)dianthracene-9-carboxylate)-k²N,N'](carbonyl)($\eta^5$-cyclopentadienyl) ruthenium(II) hexafluorophosphate as a brownish salt.

¹H NMR [acetone-d6, Me₄Si, δ/ppm (multiplicity, assignment)]: 8.71 [d, $H_{meta}$ bipyridine], 8.62 [s, $H_{para}$ anthracene], 8.49 [s, $H_{ortho}$ bipyridine], 8.22 [d, H-aromatic anthracene], 8.11 [d, H-aromatic anthracene], 7.55 [m, H-aromatic anthracene], 7.45 [d, $H_{para}$ bipyridine], 5.38 [s, $\eta^5$-cyclopentadienyl], 5.21 [m, —CH— polylactide main chain+—CH₂O bipyridine], 4.31 [q, —CH— polylactide end group], 1.55 [m, —CH₃ polylactide main chain], 1.39 [m, —CH₃ polylactide end group].

Example 5

Alternative Synthesis of an Organometallic Complex of Ruthenium that Contains a Heteroaromatic Macroligand: [(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dianthracene-9-carboxylate)-k²N, N'](triphenylphosphane)($\eta^5$-cyclopentadienyl) ruthenium(II))triflate—Compound 3

The synthesis was carried out using Schlenk techniques under nitrogen inert atmosphere and the solvents were previously dried and distilled under nitrogen atmosphere. 70 mg of [RuCp(PPh₃)₂Cl] were dissolved in anhydrous dichloromethane. Then, 450 mg of the 1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dianthracene-9-carboxylate obtained in example 2 and 24.6 mg of AgCF₃SO₃ were added. The mixture obtained was refluxed for 3 h with stirring. It was allowed to stand and the solution was filtered to remove the precipitated AgCl. Then, the product was dried under vacuum, washed with hexane and recrystallized from anhydrous dichloromethane/hexane to provide about 430 mg of the title compound [(1,1'-{1,1'-(1,1'-{2,2'-bipyridine-4,4'-diylbis(methylene)}bis(oxy)bis(1-oxopropane-2,1-diyl)) bis-(poly(lactic acid)-yl))}bis(oxy)bis(1-oxopropane-2,1-diyl)dianthracene-9-carboxylate)-k²N,N'](triphenylphosphane)($\eta^5$-cyclopentadienyl)ruthenium(II) triflate as an orange salt.

¹H NMR [acetone-d6, Me₄Si, δ/ppm (multiplicity, assignment)]: 9.51 [d, $H_{meta}$ bipyridine], 8.49 [m, H-aromatic anthracene+$H_{ortho}$ bipyridine], 7.70 [m, H-aromatic anthracene], 7.57 [m, H-aromatic phosphane], 7.57 [d, $H_{para}$ bipyridine], 7.43 [m, H-aromatic phosphane], 7.13 [m, H-aromatic phosphane], 5.35 [s, —CH₂O— bipyridine], 5.21 [m, —CH— polylactide main chain], 4.94 [s, $\eta^5$-cyclopentadienyl], 4.31 [m, —CH— polylactide end group], 1.55 [m, —CH₃ polylactide main chain], 1.39 [m, —CH₃ polylactide end group].

Example 6

Alternative Synthesis of an Organometallic Complex of Ruthenium that Contains a Heteroaromatic Macroligand: [(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dinaphthalene-2-carboxylate)-k²N, N'](triphenylphosphane)(η⁵-cyclopentadienyl) ruthenium(I) triflate—Compound 4

The synthesis was carried out using Schlenk techniques under nitrogen inert atmosphere and the solvents were previously dried and distilled under nitrogen atmosphere. 70 mg of [RuCp(PPh₃)₂Cl] were dissolved in anhydrous dichloromethane. Then, 450 mg of (1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)-bis(1-oxopropane-2,1-diyl)dinaphthalene-2-carboxylate) and 24.6 mg of AgCF₃SO₃ were added. The mixture obtained was refluxed for 3 h with stirring. It was allowed to stand and the solution was filtered to remove the precipitated AgCl. Then, the product was dried under vacuum, washed with hexane and recrystallized from anhydrous dichloromethane/hexane to provide about 420 mg of title [(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dinaphthalene-2-carboxylate)-k²N,N'](triphenylphosphane)(η⁵-cyclopentadienyl)ruthenium(II) triflate as an orange salt.

¹H NMR [acetone-d6, Me₄Si, δ/ppm (multiplicity, assignment)]: 9.51 [d, $H_{meta}$ bipyridine], 8.66 [m, H-aromatic naphthalene+$H_{ortho}$ bipyridine], 8.09 [m, $H_{para}$ bipyridine], 7.97 [d, H-aromatic naphthalene], 7.77 [d, H-aromatic naphthalene], 7.57 [m, H-aromatic naphthalene], 7.45 [t, H-aromatic phosphane], 7.34, [t, H-aromatic phosphane], 7.16 [m, H-aromatic naphthalene], 5.22 [m, —CH₂O— bipyridine+-CH-polylactide main chain], 4.95 [s, η⁵-cyclopentadienyl], 4.30 [m, —CH— polylactide end group], 1.55 [m, —CH₃ polylactide main chain+-CH₃ polylactide end group].

Example 7

Alternative Synthesis of an Organometallic Complex of Ruthenium that Contains a Heteroaromatic Macroligand: (2,2'-bipyridine-4,4'-diylbis{methylene}bis(2-{2-(2-hydroxypropanoyloxy)poly(lactic acid)-yl}propanoate)-k²N,N')(triphenylphosphane)(η⁵-cyclopentadienyl)ruthenium(H) triflate—Compound 5

The synthesis was carried out using Schlenk techniques under nitrogen inert atmosphere and the solvents were previously dried and distilled under nitrogen atmosphere. 70 mg of [RuCp(PPh₃)₂Cl] were dissolved in anhydrous dichloromethane. Then, 450 mg of the 2,2'-bipyridine-4,4'-diylbis({methylene}bis(2-{2-(2-hydroxypropanoyloxy)poly(lactic acid)-yl}propanoate) obtained in example 1 and 24.6 mg of AgCF₃SO₃ were added. The mixture obtained was refluxed for 3 h with stirring. It was allowed to stand and the solution was filtered to remove the precipitated AgCl. Then, the product was dried under vacuum, washed with hexane and recrystallized from anhydrous dichloromethane/hexane to provide about 430 mg of (2,2'-bipyridine-4,4'-diylbis{methylene}bis(2-{2-(2-hydroxypropanoyloxy)poly(lactic acid)-yl}propanoate)-k²N,N')-(triphenylphosphane)(η⁵-cyclopentadienyl) ruthenium(II) triflate as an orange salt.

¹H NMR [acetone-d6, Me₄Si, δ/ppm (multiplicity, assignment)]: 9.53 [d, $H_{meta}$ bipyridine], 8.11 [s, $H_{ortho}$ bipyridine], 7.69 [d, $H_{para}$ bipyridine], 7.60-7.10 [m, H-aromatic phosphane], 5.48 [s, —CH₂O— bipyridine], 5.20 [m, —CH— polylactide main chain], 4.97 [s, η⁵-cyclopentadienyl], 4.32 [m, —CH— polylactide end group], 1.57 [m, —CH₃ polylactide main chain], 1.40 [m, —CH₃ polylactide end group].

Example 8

Alternative Synthesis of an Organometallic Complex of Ruthenium that Contains a Heteroaromatic Macroligand: [(1,1'-{1,1'-(1,1'-{2,2'-bipyridine-4,4'-diylbis(methylene)}bis(oxy)bis(1-oxopropane-2,1-diyl))bis(poly(lactic acid)-yl)}bis(oxy)bis(1-oxopropane-2,1-diyl)di(2S,3S,4S,5R,6R)-3,4,5,6-tetrahydroxyoxane-2-carboxylate)-k²N,N'](triphenylphosphane)(η⁵-cyclopentadienyl) ruthenium(II) triflate—Compound 6

The synthesis was carried out using Schlenk techniques under nitrogen inert atmosphere and the solvents were previously dried and distilled under nitrogen atmosphere. 70 mg of [RuCp(PPh₃)₂Cl] were dissolved in anhydrous dichloromethane. Then, 450 mg of 1,1'-{1,1'-(1,1'-{2,2'-bipyridine-4,4'-diylbis(methylene)}bis(oxy)bis(1-oxopropane-2,1-diyl))bis-(poly(lactic acid)-yl))}bis(oxy)bis(1-oxopropane-2,1-diyl)di(2S,3S,4S,5R,6R)-3,4,5,6-tetrahydroxyoxane-2-carboxylate) and 24.6 mg of AgCF₃SO₃ were added. The mixture obtained was refluxed for 3 h with stirring. It was allowed to stand and the solution was filtered to remove the precipitated AgCl. Then, the product was dried under vacuum, washed with hexane and recrystallized from anhydrous dichloromethane/hexane to provide 400 mg of the title [(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)di(2S,3S,4S,5R,6R)-3,4,5,6-tetrahydroxyoxane-2-carboxylate)-k²N,N'](triphenylphosphane)(η⁵-cyclopentadienyl)ruthenium(II) triflate as an orange salt.

¹H NMR [acetone-d6, Me₄Si, δ/ppm (multiplicity, assignment)]: 9.53 [d, $H_{meta}$ bipyridine], 8.10 [s, $H_{ortho}$ bipyridine], 7.67-7.11 [m, H-aromatic phosphane+$H_{para}$ bipyridine], 5.49-5.31 [m, H glucuronic ester], 5.20 [m, —CH₂O-bipyridine+-CH-polylactide main chain], 4.96 [s, η⁵-cyclopentadienyl], 4.30 [m, —CH— polylactide end group+H glucuronic ester], 3.47-3.29 [m, H glucuronic ester], 1.55 [m, —CH₃ polylactide main chain], 1.39 [m, —CH₃ polylactide end group].

Example 9

Synthesis of a Macromolecular 1-({1-({1-(benzyloxy)-1-oxopropane-2-yl}oxy)-1-(poly-(lactic acid))}-1-oxopropane-2-yl-4-(diphenylphosphino)benzoate The synthesis was carried out using Schlenk techniques under nitrogen inert atmosphere and the solvents were previously dried and distilled under nitrogen atmosphere. A mixture of 1 g of 3,6-dimethyl-1,4-dioxane-2,5-dione, 28.25 mg of dimethylaminopyridine and 11.98 µl of phenylmethanol was heated at 135° C. in an oil bath and with stirring. Once the 3,6-dimethyl-1,4-dioxane-2,5-dione was melted, it was allowed to stay for 5 minutes. After this period, the reaction was quenched with the addition of an excess of a methanol/water mixture. Then, the product was precipitated in about 50 ml of a methanol/water mixture. The solvent was evaporated in vacuum and the product was washed with diethyl ether and dried under vacuum. Then, 270 mg of this polymer were dissolved in anhydrous THF and 10 µl of triethylamine was added. The reaction continued for 1 h. After this period 23 mg of 4-(diphenylphosphane)benzoic acid were added and the reaction continued at the THF reflux temperature until complete removal of the water formed in the reaction using a Dean-Stark apparatus. Finally, the product was dried under vacuum to provide 700 mg of the title compound as a white product.

$^1$H NMR [CDCl$_3$, Me$_4$Si, δ/ppm (multiplicity, assignment)]: 7.41-7.20 [m, H-aromatic benzyl and phosphane], 5.19 [m, —CH— polylactide main chain], 4.39 [q, —CH— polylactide end group], 1.52 [m, —CH$_3$ polylactide main chain], 1.41 [m, —CH$_3$ polylactide end group].

Example 10

Synthesis of an Organometallic Complex of Iron that Contains a Macromolecular Phosphane: [1-({1-({1-(benzyloxy)-1-oxopropane-2-yl}oxy)-1-(poly-(lactic acid))}-1-oxopropane-2-il4-(diphenylphosphino)benzoate-k$^1$P](carbonyl)(iodide)(η$^5$-cyclopentadienyl)iron(II)—Compound 7

The synthesis was carried out using Schlenk techniques under nitrogen inert atmosphere and the solvents were previously dried and distilled under nitrogen atmosphere. 810 mg of [FeCp(CO)$_2$I] were dissolved in anhydrous acetone. Then, 900 mg of 4-(diphenylphosphane)benzoic acid (BZA) were added. The mixture was irradiated with UV (230V, 300 W lamp) for 3 h with stirring. It was allowed to stand and the solution was filtered; then the solvent of the filtrate was evaporated. The compound obtained was washed with hexane and recrystallized from anhydrous dichloromethane/hexane to provide the desired compound [FeCp(P(Ph$_2$)(BZA))(CO)I]. 95 mg of this compound were dissolved in about 50 ml de THF anhydrous and 50 µl of trimethylamine were added. The reaction continued for 1 h. After this period, 420 mg of the desired polymer were added and the reaction continued at the THF reflux temperature until complete removal of the water formed in the reaction using a Dean-Stark apparatus. Finally the product was dried under vacuum to provide 390 mg of the title compound [1-({1-({1-(benzyloxy)-1-oxopropane-2-yl}oxy)-1-(poly-(lactic acid))}-1-oxopropane-2-yl4-(diphenylphosphino)benzoate-k$^1$P](carbonyl)(iodide)(η$^5$-cyclopentadienyl)iron(II) as a brownish green neutral solid compound.

$^1$H NMR [dmso-d6, Me$_4$Si, δ/ppm (multiplicity, assignment)]: 7.90-7.30 [m, H aromatics phosphane+H aromatics benzyl], 5.1 [m, η$^5$-cyclopentadienyl+-CH-polylactide main chain+-CH$_2$O benzyl], 4.63 [q, —CH— polylactide end group], 1.24 [m, —CH$_3$ polylactide main chain], 1.24 [m, —CH$_3$ polylactide end group].

Example 11

Synthesis of a Macromolecular Phosphane: tris(1-{1-(1-hidroxypropanoyloxy)poly(lactic acid)-yl}propanoate)phosphane The synthesis was carried out using Schlenk techniques under nitrogen inert atmosphere and the solvents were previously dried and distilled under nitrogen atmosphere. A mixture of 1 g of (3S)-cis-3,6-dimethyl-1,4-dioxane-2,5-dione, 56.5 mg of dimethylaminopyridine and 30 mg of tris(hidroxymethyl)phosphine was warmed a 120° C. in an oil bath under stirring. After melting of the (3S)-cis-3,6-dimethyl-1,4-dioxane-2,5-dione, it was allowed to stay for 5 minutes, and after this period the reaction was quenched with the addition of an excess of a methanol/water mixture. Then, the product was precipitated in about 50 ml of a methanol/water mixture. The solvent was evaporated under vacuum and the product obtained was washed with diethyl ether and dried under vacuum, to provide about 900 mg of the title compound as a white product.

$^1$H NMR [CDCl$_3$, Me$_4$Si, δ/ppm (multiplicity, assignment)]: 5.16 [m, —CH— polylactide main chain], 4.58 [s, —CH$_2$O phosphine], 4.36 [q, —CH— polylactide end group], 1.58 [m, —CH$_3$ polylactide main chain], 1.50 [m, —CH$_3$ polylactide end group].

Example 12

Synthesis of an Iron Organometallic Complex Containing a Macromolecular Phosphane: [tris(1-{1-(1-hidroxypropanoyloxy)poly(lactic acid)-yl}propanoate)phosphane-k$^1$P] (carbonyl)(iodide) (η$^5$-cyclopentadienyl)iron(II)—Compound 8

The synthesis was carried out using Schlenk techniques under nitrogen inert atmosphere and the solvents were previously dried and distilled under nitrogen atmosphere. 40 mg of [FeCp(CO)$_2$I] were dissolved in anhydrous acetone. Thereafter, 445 mg of tris(1-{1-(1-hidroxypropanoyloxy)poly(lactic acid)-yl}propanoate)phosphane prepared in the above example were added. The mixture obtained was irradiated by UV (230V lamp, 300 W) for 8 hours under stirring and nitrogen atmosphere. The solution was allowed to stand and filtered; then, the filtrate solvent was evaporated. The compound obtained was washed with hexane and recrystallized with anhydrous acetone/n-hexane, thus providing about 450 mg of the title compound as a brownish green neutral solid compound.

$^1$H NMR [CDCl$_3$, Me$_4$Si, δ/ppm (multiplicity, assignment)]: 5.16 [m, —CH$_2$O-phosphine, —CH— polylactide main chain], 4.63 [s, η$^5$-cyclopentadienyl], 4.31 [m, —CH— polylactide end group], 1.57 [m, —CH$_3$ polylactide main chain], 1.50 [m, —CH$_3$ polylactide end group]

Example 13

Alternative Synthesis of a Ruthenium Organometallic Complex Containing a Macromolecular Phosphane: [(1-({1-({1-(benzyloxy)-1-oxopropane-2-yl}oxy)-1-(poly-(lactic acid)}-1-oxopropane-2-yl)-4-(diphenylfosfino)benzoate-k$^1$P](2-benzoylpyridine)-k$^2$N,O)(η$^5$-cyclopentadienyl)ruthenium(II)triflate—Compound 9

137 mg of ({1-({1-(benzyloxy)-1-oxopropane-2-yl}oxy)-1-(poly-(lactic acid))}-1-oxopropane-2-yl) were dissolved in about 50 mL of anhydrous THF and 50 µl of triethylamine were added. The reaction continued for 1 h. After this period, 68 mg of [(2-benzoylpyridine)-k$^2$N,O] [(4-(diphenylfosfino-benzoate))-k$^1$P](η$^5$-cyclopentadienyl)ruthenium(II) triflate were added and the reaction continued at THF reflux temperature until complete removal of the water formed throughout the reaction using a Dean-Stark apparatus. The product was dried under vacuum to provide 93 mg of the title compound as a violet solid product.

$^1$H NMR [acetone-d6, Me$_4$Si, δ/ppm (multiplicity, assignment)]: 9.89 [d, H$_{ortho}$ pyridine], 8.30 [d, H$_{meta}$ pyridine], 8.05 [t, H$_{para}$ pyridine], 7.95 [d, H-aromatic phosphane], 7.68 [m, H$_{meta}$ pyridine+], 7.60-7.20 [m, H-aromatic phosphane+H-aromatic benzyl], 5.20 [m, —CH$_2$-benzyl polylactide end group, —CH— polylactide main chain], 4.88 [s, η5-cyclopentadienyl]; 4.32 [m, —CH— polylactide end group], 1.55 [m, —CH$_3$ polylactide main chain], 1.47 [m, —CH$_3$ polylactide end group].

The monomodal character of the macromolecule distribution, represented in the FIGS. 2a to 2f, shows a dispersity of 1.1 for the compound 6, of 1.2 for the compounds 2, 3 and 5, of 1.3 for the compound 4 and of 1.4 for the compound 1, highlighting the presence of a single population/species of compound (monomodal character) with very similar molecular mass values (dispersity around 1).

II—Biological Activity

Example 14

Cell Viability Inhibition Assays In Vitro

By way of example the cytotoxic activity of the compounds 1, 2, 3, 4, 5 and 6 was studied, by determining the concentration required for 50% inhibition of cell viability (IC$_{50}$), parameter used to assess the inhibition of the in vitro activity, in human tumor lines for some compounds of the present invention.

a) The cytotoxic activity of the compounds 5 and 6 was assessed in human tumor cells of MCF-7 breast adenocarcinoma proceeding as follows for each the test compound:

The culture of human breast carcinoma (MCF-7; ATCC) cell line was carried out in DMEM (Gibco) medium containing GlutaMax I and was supplemented with 10% FBS and 1% penicillin-streptomycin and kept at 37° C. in a humidified atmosphere containing 5% CO$_2$.

The cell culture was made in flasks containing the medium appropriate to cell proliferation and allowing cell adhesion.

Upon reaching the required confluence, the cells were harvested through the addition of a 0.05% trypsin-EDTA solution (Gibco®). The cell viability was assessed by the MTT assay which measures the reduction of 3-(4,5-dimethylthiazol-2-yl)-2,5-diphenyltetrazolium bromide (MTT) to blue formazan by the viable cells. For this, the cells were seeded in 200 μl of complete cell medium in 96-well plates. Cell density was 2×10$^4$ viable cells (MCF-7) per well.

Cells were left to adhere for 24 h, followed by the addition of various dilutions in medium (200 μl) of the test compound. The test compound was first solubilized in DMSO and then in the cell medium and added to the cells at concentrations 1-100 μM. The final DMSO concentrations in the medium were lower than 0.5%. After 24 h and 72 h incubation, 37° C./5% CO$_2$, the medium was substituted by 200 μl of the MTT solution (0.5 mg/ml in phosphate buffer—PBS). After 3-4 h incubation, the MTT solution was removed and the formazan crystals formed by the viable cells were dissolved in DMSO (200 μl). The cell viability was assessed measuring the absorbance at 570 nm, using the plate spectrophotometer. The cytotoxicity of the test compound was quantified calculating the drug concentration that inhibits the growth of 50% of cells (IC$_{50}$) (GraphPad Prism software). The assessment was carried out with at least two independent experiments, each comprising six replicates per concentration. Dose-response curves of cell viability after 24 h and 72 h of incubation, respectively, are represented in the graphs of the FIGS. 3a and 3b. The results obtained show clearly that both the compounds 5 and 6 are cytotoxic for the MCF-7 cell line in the micromolar range. In addition, there is a clear dose-response relationship.

b) The cytotoxic activity of the compounds 5 and 6 was assessed in human A2780 ovarian carcinoma cells and in cells of MDA-MB-231 human breast carcinoma proceeding as follows for each of the test compound:

The cultures of human breast (MDA-MB-231; ATCC) and ovarian (A2780, ATCC) carcinoma cell lines, were carried out in DMEM (Gibco) medium containing GlutaMax I (MDA-MB-231) or RPMI (A2780) and were completed with 10% FBS and 1% penicillin-streptomycin and kept at 37° C. in a humidified atmosphere containing 5% de CO$_2$.

The cell culture was made in flasks containing the medium appropriate to cell proliferation and allowing cell adhesion.

Upon reaching the required confluence, the cells were harvested through addition of a 0.05% trypsin-EDTA solution (Gibco®). The cell viability was assessed by the MTT assay which measures the reduction of 3-(4,5-dimethylthiazol-2-yl)-2,5-diphenyltetrazolium bromide (MTT) to blue formazan by the viable cells. For this, the cells were seeded in 200 μl of complete cell medium in 96-well plates. Cell density was 2×10$^4$ viable cells (MDA-MB-231 and A2780) per well.

Cells were left to adhere for 24 h, followed by the addition of various dilutions in medium (200 μl) of the test compound. The test compound was first solubilized in DMSO and then in the cell medium and added to the cells at concentrations 1-100 μM. The final DMSO concentrations in the medium were lower than 0.5%. After 24 h and 72 h incubation, 37° C./5% CO$_2$, the medium was substituted by 200 μl of the MTT solution (0.5 mg/ml in phosphate buffer—PBS). After 3-4 h incubation, the MTT solution was removed and the formazan crystals formed by the viable cells were dissolved in DMSO (200 μl). Cell viability was assessed measuring the absorbance at 570 nm, using a plate spectrophotometer.

Figure 4:
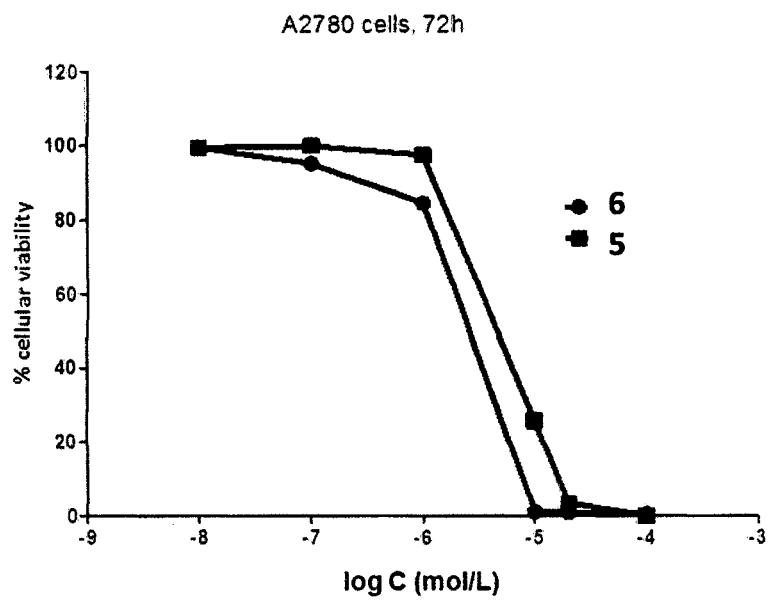
FIGS. 4a) and 4b) are dose-response graphs representing the cytotoxic activity of the compounds 5 and 6, after 72 h of incubation, against human ovarian carcinoma cells A2780 and against human breast carcinoma cells MDA-MB-231, respectively.
Figure 4:
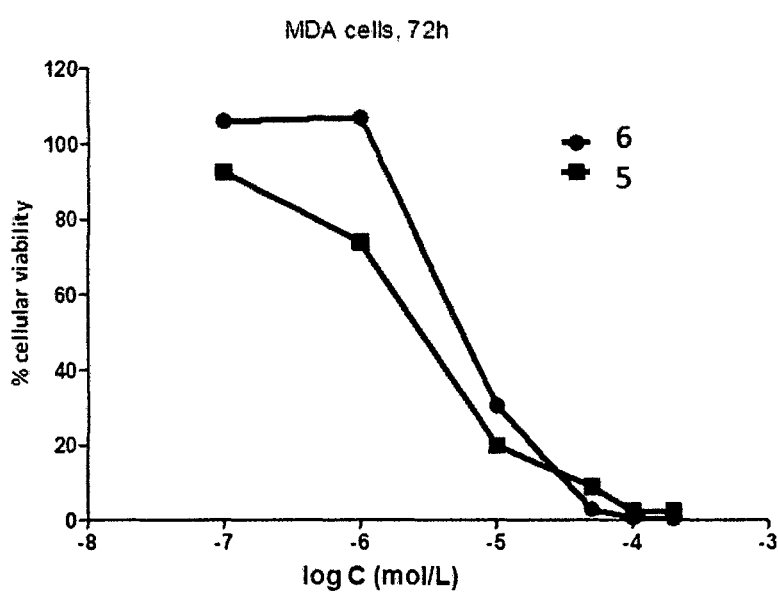
Figure 5:
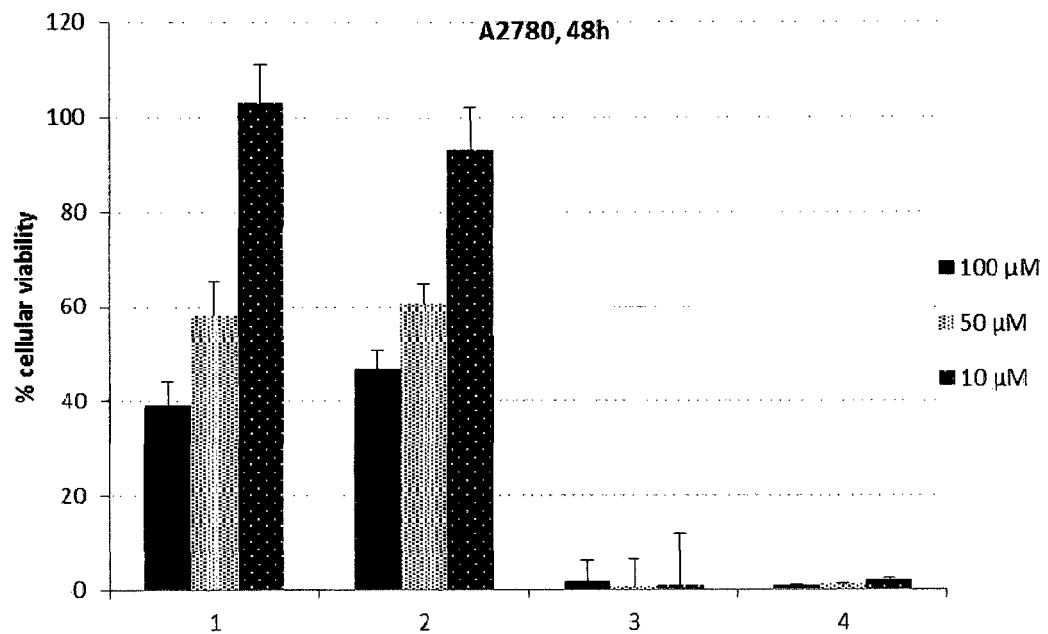
FIGS. 5a) to 5d) are graphs representing the cytotoxic activity of the compounds 1, 2, 3, 4 against human tumor cells after 48 h of incubation, against A2780 ovarian, MCF-7 breast, U87 glioma and A345 melanoma human tumour lines, respectively.
Figure 5:
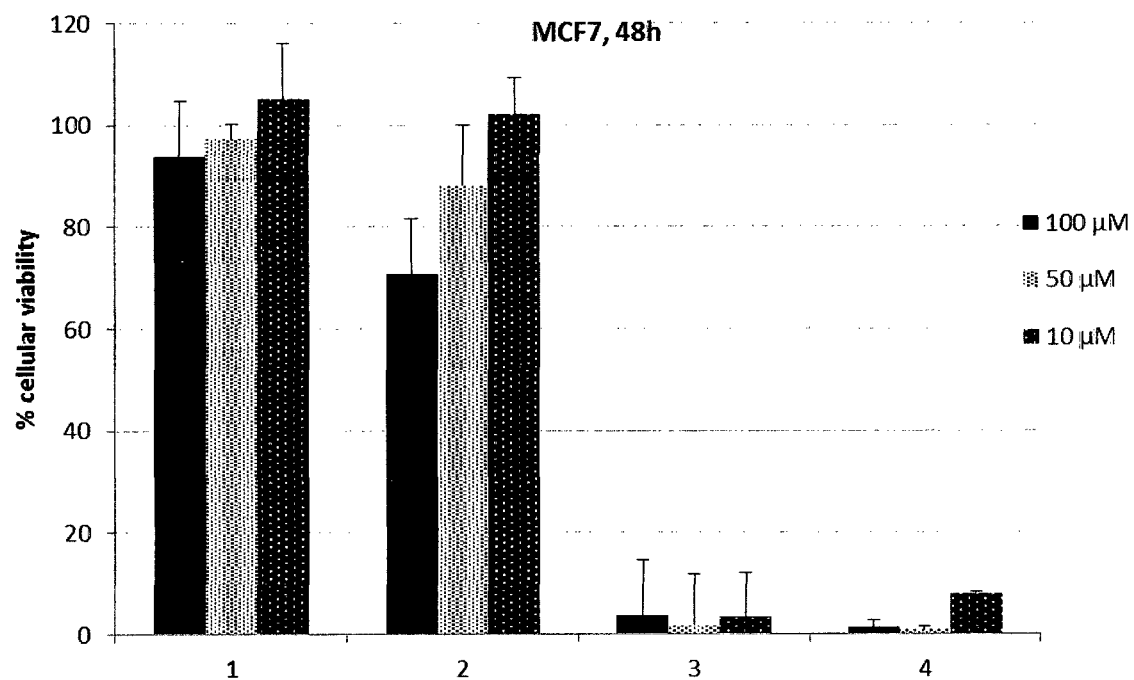
Figure 5:
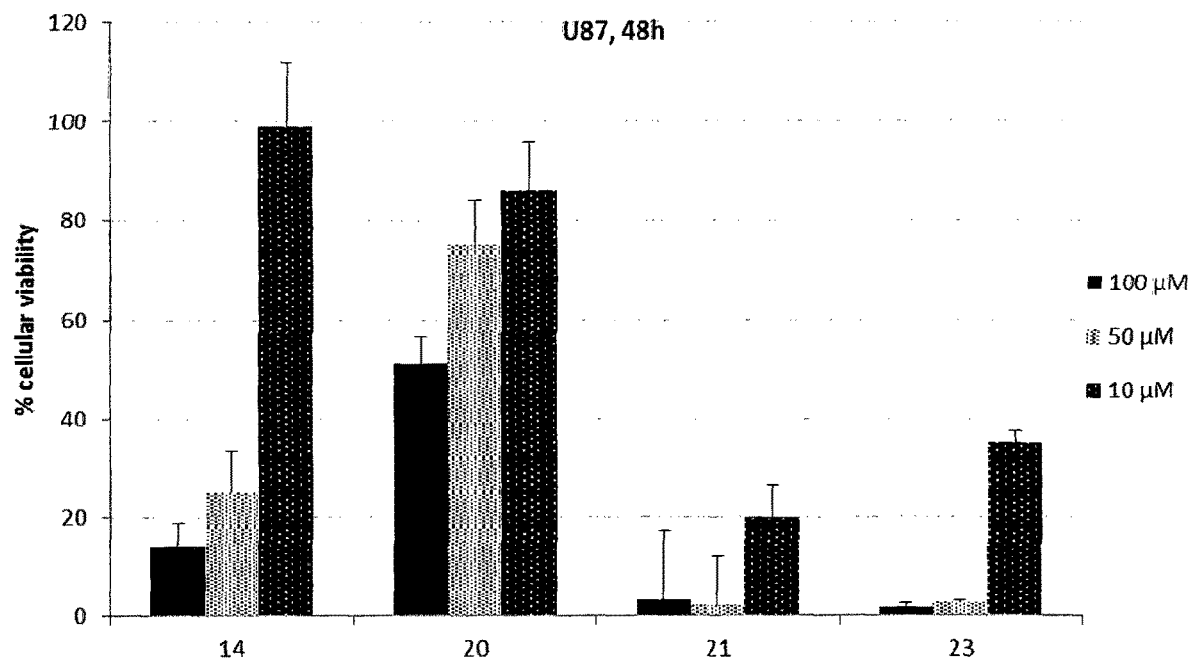
Figure 5:
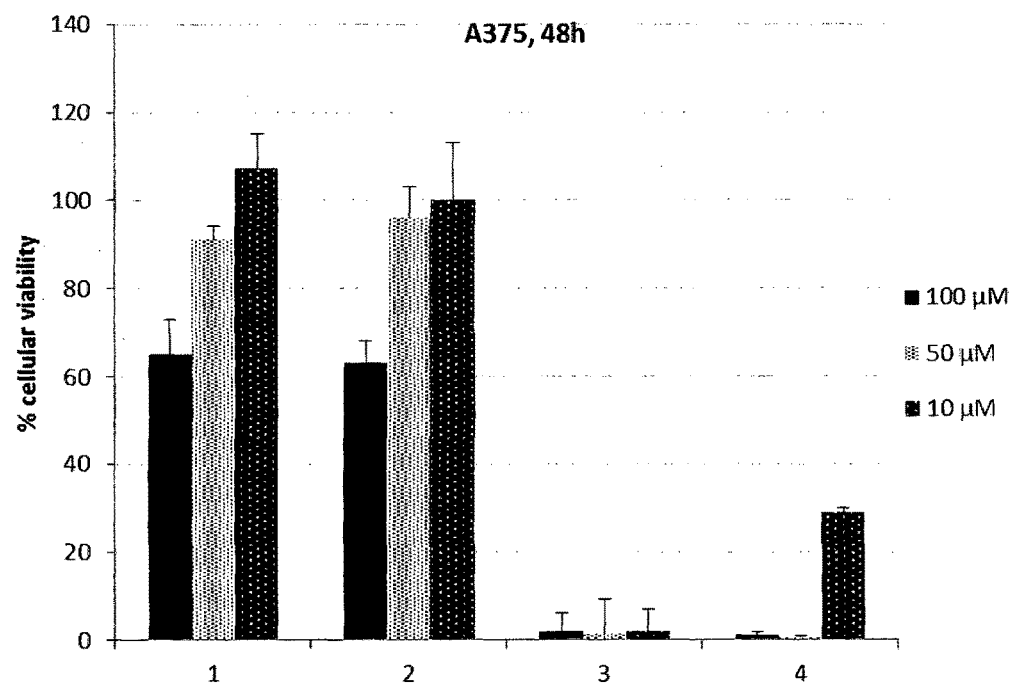

The cytotoxicity of the test compound was quantified calculating the drug concentration that inhibits the growth of 50% of cells (IC$_{50}$) (GraphPad Prism software). The assessment was carried out with at least two independent experiments, each comprising six replicates per concentration. Dose-response curves of cell viability, after a 72 h incubation, are represented in the graphs of the FIGS. 4a and 4b. The results obtained show clearly that both the compounds 5 and 6 are cytotoxic for the MDA-MB-231 and A2780 cell lines in the micromolar range. In addition, there is a clear dose-response relationship.

c) The cytotoxic activity of the compounds 1, 2, 3 and 4 was assessed in tumor cells of human ovarian A2780, breast MCF-7, glioma U87 and melanoma A345 tumor lines proceeding as follows for each of the test compound:

The cultures of human breast (MCF-7; ATCC), glioma (U87, ATCC) and melanoma (A345; ATCC) cell lines were carried out in DMEM (Gibco®) medium containing GlutaMax I (MCF-7; U87; A345) or RPMI (A2780) and were completed with 10% FBS and 1% penicillin-streptomycin and kept at 37° C. in a humidified atmosphere containing 5% de CO$_2$. The cell culture was made in flasks containing the medium appropriate to cell proliferation and allowing the cell adhesion. Upon reaching the required confluence, the cells were harvested through addition of a 0.05% trypsin-EDTA solution (Gibco®). The cell viability was assessed by the MTT assay which measures the reduction of 3-(4,5- dimethylthiazol-2-yl)-2,5-diphenyltetrazolium bromide (MTT) to blue formazan by the viable cells. For this, the cells were seeded in 200 µl of complete cell medium in 96-well plates. Cell density was $2\times10^4$ viable cells (MCF-7) per well. Cells were left to adhere for 24 h, followed by the addition of various dilutions in medium (200 µl) of the test compound. The test compound was first solubilized in DMSO and then in the cell medium and added to the cells at concentrations 1-100 µM. The final DMSO concentrations in the medium were lower than 0.5%. After 24 h and 72 h incubation, 37° C./5% $CO_2$, the medium was substituted by 200 µl of the MTT solution (0.5 mg/ml in phosphates-PBS buffer). After a 3-4 h incubation, the MTT solution was removed and the formazan crystals formed by the viable cells were dissolved in DMSO (200 µl). The cell viability was assessed measuring the absorbance at 570 nm, using the plate spectrophotometer. The cytotoxicity of the test compound was quantified calculating the drug concentration that inhibits the growth of 50% of cells ($IC_{50}$) (GraphPad Prism software). The assessment was carried out with at least two independent experiments, each comprising six replicates per concentration. The results obtained after 48 h of incubation are shown in the graphs of the FIGS. 5a a 5d, respectively, demonstrating that all the compounds are cytotoxic for all the four cell lines. Compounds 3 and 4 (containing the triphenylphosphane ligand), are the most active (in relation to the compounds 1 and 2, which contain the ligand CO). It should be noted that the values obtained for the highly deadly line of glioma are remarkable (the value found in the literature for cisplatin is 130±53 µM (O. Patapova, A. Haghighi, F. Bost, C. Liu, M. J. Birrer, R. Gjerset, D. Mercota, J. Biol. Chem. 1997, 272:14041-14044).

Such as represented in FIGS. 1a to 1f, the relative variation (%) of the absorbance at fixed wavelength over time (>24 h) for the compounds 1, 2, 3, 4, 5 and 6, respectively, in the 5% DMSO mixture: 95% of cell medium show the appropriate chemical stability in an aqueous medium of the compounds.

The results are among the lower values of cytotoxicity for compounds of the "piano-stool" type (e.g. P. C. A. Bruijn-incx, P. J. Sadler, In: in R. Van Eldik, C. D. Hubbard (Eds), Advances in Inorganic Chemistry, 61, Academic Press, London, 2009, pp. 1-61) and the compounds display activity in a range of micromolar concentrations, and in most cases are better than the reference compound, cisplatin, as shown in Table 1 below. Table 1 shows $IC_{50}$ values, the concentration required for 50% inhibition of the cell viability in MCF-7, A2780 and MDA-MB-231 cells, corresponding to two new compounds, compounds 5 and 6, whose dose-response curves of cell viability are represented in FIGS. 3b), 4a) and 4b).

TABLE 1

| | $IC_{50}$ after a 72 h incubation | | |
|---|---|---|---|
| | MCF-7(µM) | A2780 (µM) | MDA-MB-231(µM) |
| Compound 5 | 4.09 ± 1.97 | 3.4 ± 1.3 | 2.7 ± 0.55 |
| Compound 6 | 4.62 ± 1.15 | 2.20 ± 0.85 | 5.96 ± 3.25 |
| Cisplatin | 28 ± 6.0 | 2.0 ± 0.10 | 39 ± 5.0 |

Figure 3:
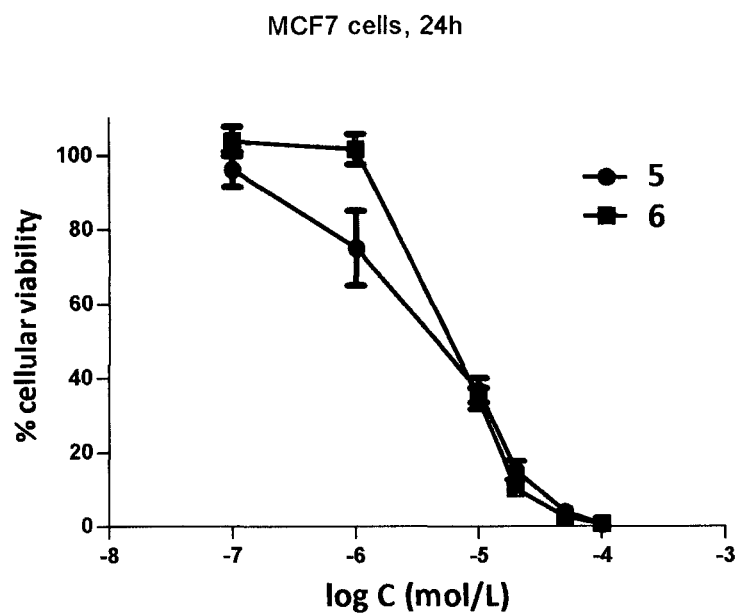
FIGS. 3a) and 3b) are graphs representing the cytotoxic activity of the compounds 5 and 6 against human tumor cells of MCF-7 breast adenocarcinoma, after 24 h and 72 h of incubation, respectively.
Figure 3:
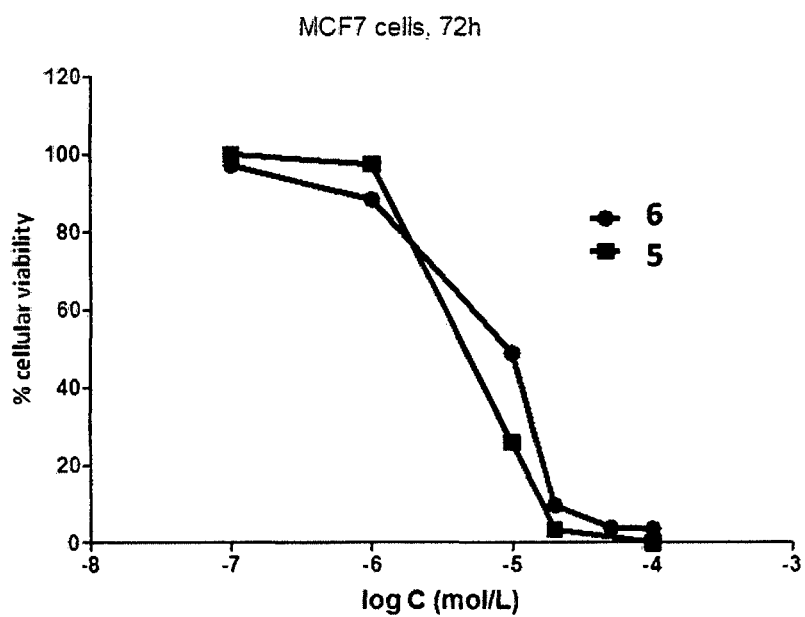

Table 2 below shows the values for $IC_{50}$, in MCF-7 cells, corresponding to compounds 5 and 6, whose dose-response curves of cell viability are represented in FIG. 3a).

TABLE 2

| | $IC_{50}$ after a 24 h incubation MCF-7 (µM) |
|---|---|
| Compound 5 | 4.25 ± 1.15 |
| Compound 6 | 5.00 ± 1.65 |

Once reached the tumor tissue and due to the enhanced permeability and retention (EPR) effect the compounds can accumulate there, increasing the drug efficiency and thereby allowing to reduce the number of treatment doses and the time spacing which represents an advantage of great importance in chemotherapy.

Figure 6:
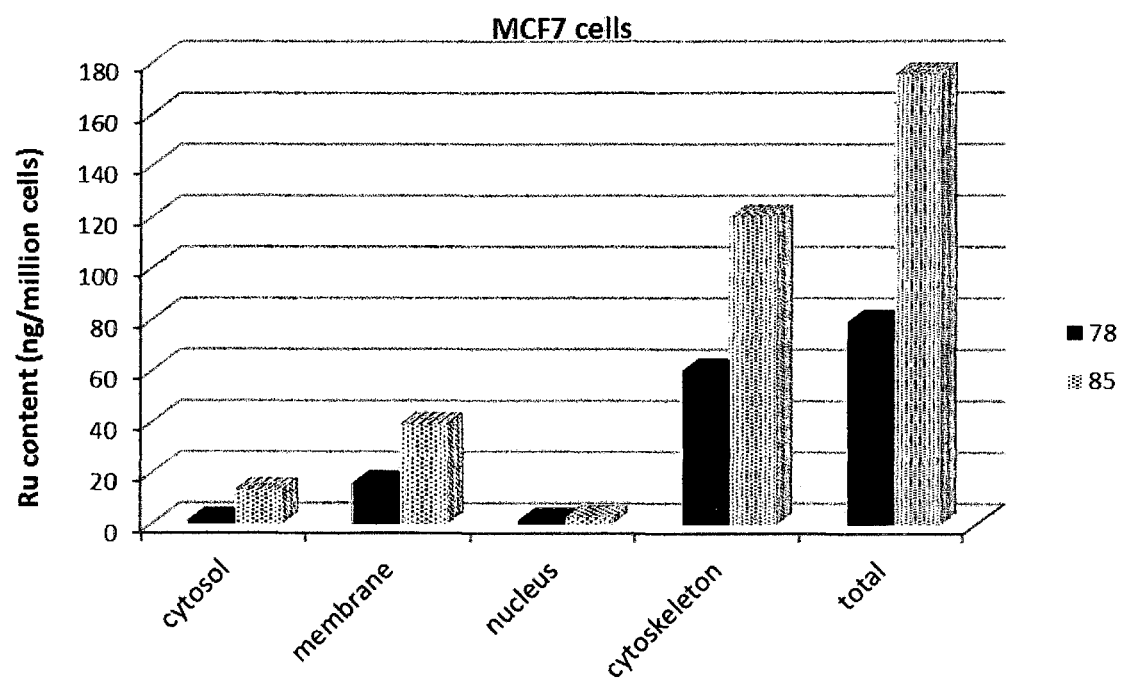
FIG. 6 is a graph representing the cellular distribution for the compounds 5 and 6 against human MCF-7 breast tumor cells after 24 h of incubation.

The cell distribution studies of these compounds in tumor cells show that they are predominantly located on the cytoskeleton, nucleus and/or cytoplasm of these cells, indicating that they accumulate within the cell, bringing great expectations for its use in targeted therapy, namely to intracellular targets. The graph of FIG. 6 shows the cell distribution of the compounds 5 and 6 in MCF-7 human breast tumor cells after a 24 h incubation being the differences observed related with the molecule of biological interest (—OH in compound 5 vs. sugar in compound 6) used in each of the different compounds.

From the evidence, it can be concluded that the drugs according to the present invention including molecules recognized by the tumor target are able to reach tumor cells with high precision. The efficiency of these drugs is also increased due to the remaining product of polymer biodegradation, which contains the organometallic unit, also show cytotoxicity against tumor cells. This feature of the compounds of the present invention can also be the key to overcome the terrible chemotherapy side effects caused by the drugs currently in use.

The ability to act at the metastases level is critical, since the vast majority of deaths caused by cancer is due to the metastases and not to the primary tumor. It is expected that the compounds according to the present invention show also favourable properties towards the fight against metastases, in addition to the performance at primary tumor level, taking into account, in the first place, the excellent results obtained in vitro in highly metastatic cell lines, such as MDA-MB-231, and in the second place, the results from the in vivo studies in nude mice using low-molecular weight compounds (i.e. not including polymers on its structure) already synthesized by us. The results obtained in nude mice N:NIH (S)II-nu/nu, to which a tumor (MDA-MB-231) was induced in the mammary gland, showed that an injection of 2.5 mg/kg per day of the test drug, for 10 days, induces tumor suppression in about 50% as regards the control mice. The most important result is the absence of metastases within the main organs (lungs, kidneys, liver, and heart) after the treatment, while all the control mice showed metastases. These results suggest that this drug can act not only on the primary tumor, but also through the inhibition of the metastatic behaviour, probably interfering with tumor angiogenesis.

In addition, the compounds of the present invention cause cell death by apoptosis, which is a controlled cell death mechanism that prevents lysis of the affected cell to the surroundings, apparently by a mitochondrial pathway, as proven by apoptosis assays as described below.

Example 15

Apoptosis Assay

To assay the apoptosis induced by the compounds 5 and 6 in human cells of MCF-7 breast cancer, in comparison to untreated cells, a kit for the detection of the apoptotic process was used, the Human Apoptosis Array which provides a rapid and sensitive method to simultaneously detect the relative levels of expression of 35 apoptosis process-related proteins (control cells indicate a 100% level of expression), proceeding according to the manufacturer's instructions.

Figure 7:
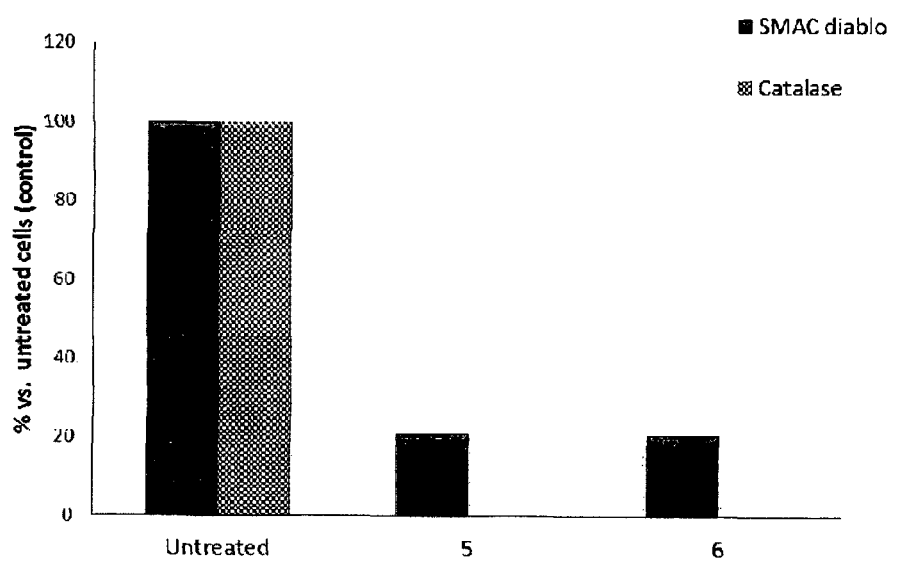
FIG. 7 is a graph representing the results of the apoptotic processes in human MCF-7 breast tumor cells untreated and treated with the compounds 5 and 6.

After a 24 h incubation with the compounds 5 and 6 a decrease in the expression of the test catalase and SMAC diablo proteins was observed suggesting that the apoptosis process is induced through the intrinsic-mitochondrial pathway. The intrinsic pathway is triggered by intracellular or extracellular stress. The signals that are transduced in response to these stimuli converge mainly to the mitochondria. This organelle integrates the cell death stimuli, inducing mitochondrial permeabilization and consequent release of pro-apoptotic molecules present therein. These results also suggest that the complexes induce high levels of oxidative stress in the tumor cells. The results obtained are represented in the graph of FIG. 7.

Example 16

Determination of the Mechanism of Cell Death Induced by Compounds 5 and 6

The type of cell death induced by of compounds 5 and 6 in MCF-7 cancer cell line after 48 h of incubation at a 10 µM concentration was determined by the Annexin V/Propidium iodide (PI) cytometry-based assay. This assay is widely used to determine if cells are viable, apoptotic, or necrotic through differences in plasma membrane integrity and permeability. All in all, Annexin V/PI is a commonly used approach for studying cell death (Rieger et al. 2011).

Figure 8:
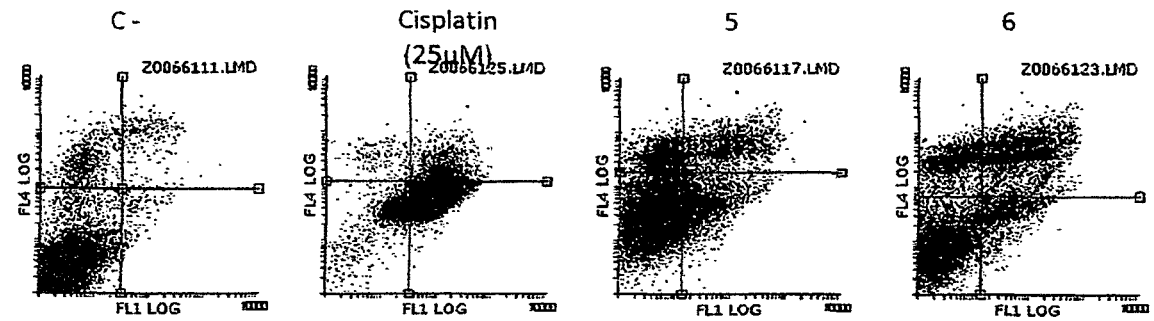
FIG. 8 are graphs representing the results of the assays for determining the type of mechanism of cell death induced by the compounds 5 e 6 MCF-7 against tumor cells, after a 48 h incubation.

Results have shown that the incubation of compounds 5 and 6 led to an increase in the percentage of Anexin V stained cells (FIG. 8) in comparison to the control. Annexin V a marker of early apoptosis. Indicating that, in this case, the type of cell death induced by these compounds is apoptosis. As for the double staining with both markers, it suggests late apoptosis. Cisplatin was used as a positive control since it is known to induce apoptosis.

Example 17

Effect of Compounds 5 and 6 on Cytoskeleton

Taking into account previous results that suggested that both compounds 5 and 6 interacted with the cytoskeleton (FIG. 9), an immunofluorescence technique was performed in the MCF-7 cancer cell line.

Figure 9:
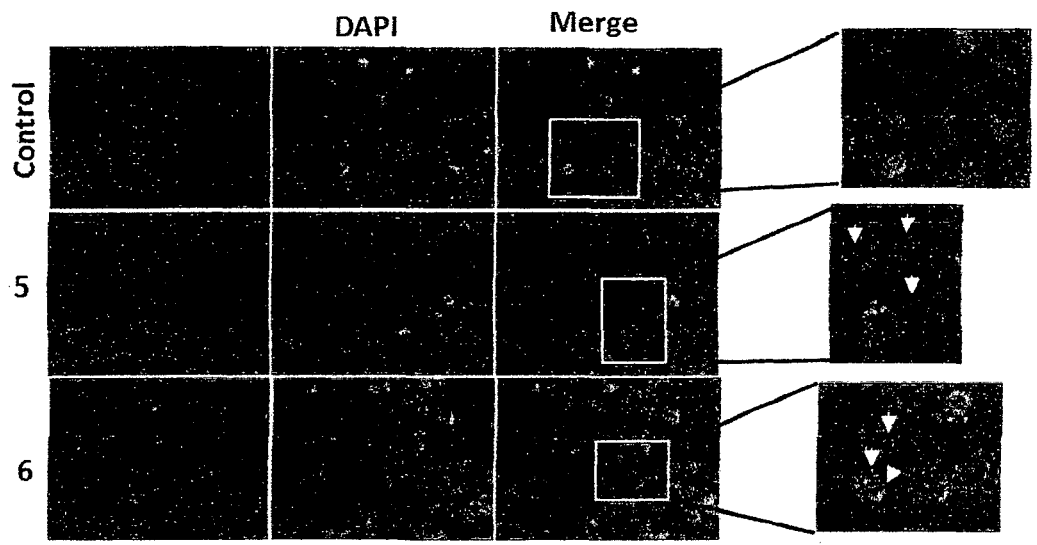
FIG. 9 is a graph representing the results of the immunofluorescence assays in MCF-7 human breast cancer cells to determine the effect of the compounds 5 and 6 on the cytoskeleton.

In this immunofluorescence assay, Alexa Fluor 488® phalloidin, which is a high-affinity filamentous actin (F-actin) probe conjugated to the green-fluorescent Alexa Fluor® 488 dye was used. In order to obtain nuclear staining DAPI (blue) was used (FIG. 9). In control cells the integrity of the F-actin filaments could be observed, where a clear delimitation of cells is seen. In contrast, in cells incubated with compounds 5 and 6, cytoskeleton loses its organization. Moreover, the appearance of some dotted-like structures inside the nuclei of cells treated with both compounds can be also detected.

The invention claimed is:

1. Macromolecular transition metal complexes characterized by being:

(2,2' bipyridine-4,4'-diylbis{methylene}bis(2-{2-(2-hydroxypropanoyloxy)poly(lactic acid)-yl}propanoate)-k$^2$N,N')(carbonyl)($\eta^5$-cyclopentadienyl)ruthenium(II) hexafluorophosphate;

[(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dianthracene-9-carboxylate)-k$^2$N,N'](carbonyl)($\eta^5$-cyclopentadienyl)ruthenium(II) hexafluorophosphate;

[(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dianthracene-9-carboxylate)-k$^2$N,N'](triphenylphosphane)($\eta^5$-cyclopentadienyl)ruthenium(II)) triflate;

[(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)dinaphthalene-2-carboxylate)-k$^2$N,N'](triphenylphosphane)($\eta^5$-cyclopentadienyl)ruthenium(II) triflate;

(2,2'-bipyridine-4,4'-diylbis{methylene}bis(2-{2-(2-hydroxypropanoyloxy)poly(lactic acid)-yl} propanoate)-k$^2$N,N)(triphenylphosphane)($\eta^5$-cyclopentadienyl)ruthenium(II) triflate;

[(1,1'-{1,1'-(1,1'-{2,2'-bipyridine-4,4'-diylbis(methylene)}bis(oxy)bis(1-oxopropane-2,1-diyl))bis(poly(lactic acid)-yl))}bis(oxy)bis(1-oxopropane-2,1-diyl)di(2 S,3 S,4 S, 5R, 6R)-3,4,5,6-tetrahydroxyoxane-2-carboxylate)-k$^2$N,N'](triphenylphosphane)($\eta^5$-cyclopentadienyl)-ruthenium(II) triflate;

[1-({1-({1-(Benzyloxy)-1-oxopropane-2-yl} oxy)-1-(poly(lactic acid))}-1-oxopropane-2-yl-4-(diphenylphosphino)benzoate-k$^1$P](carbonyl)(iodide)($\eta^5$-cyclopentadienyl)iron(II);

[Tris(1-{1-(1-hydroxypropanoyloxy)poly(lactic acid)-yl}propanoate)phosphane-k'P] (carbonyl)(iodide)($\eta^5$-cyclopentadienyl)iron(II); or

[(1-({1-({1-(Benzyloxy)-1-oxopropane-2-yl} oxy)-1-(poly(lactic acid)))}-1-oxopropane-2-yl)-4-(diphenylphosphino)benzoate-k$^1$P]((2-benzoylpyridine)-k$^2$N,O)($\eta^5$-cyclopentadienyl) ruthenium(II) triflate.

2. A pharmaceutical composition comprising a pharmaceutically effective amount of at least one macromolecular transition metal complex, in accordance with claim 1.

3. The pharmaceutical composition of claim 2, wherein the pharmaceutically effective amount of at least one macromolecular transition metal complex, in accordance with claim 1 in combination with other active ingredients and/or pharmaceutically acceptable vehicles and/or excipients.

4. The pharmaceutical composition according to claim 2 for use in cancer therapy and/or cancer prevention, as Antitumoral agent in the treatment of solid tumors, liquid tumors and/or metastases and/or as radiosensitizer agent.

5. The macromolecular transition metal complexes according to claim 1 for use in cancer therapy and/or cancer prevention, as antitumoral agent in the treatment of solid tumors, liquid tumors and/or metastases and/or as radiosensitizer agent.

6. The pharmaceutical composition according to any one of the claims 2-4 or the macromolecular transition metal complexes for use in cancer therapy and/or cancer prevention, as antitumoral agent in the treatment of solid tumors, liquid tumors and/or metastases and/or as radiosensitizer agent according to claim 5 characterized in that said pharmaceutical composition or macromolecular transition metal complex is for use via topical, intravenous, subcutaneous or intraperitoneal administration.

* * * * *